US008796040B2

(12) United States Patent
Aizawa et al.

(10) Patent No.: US 8,796,040 B2
(45) Date of Patent: Aug. 5, 2014

(54) SYSTEM AND METHOD OF QUANTITATIVELY DETERMINING A BIOMOLECULE, SYSTEM AND METHOD OF DETECTING AND SEPARATING A CELL BY FLOW CYTOMETRY, AND FLUORESCENT SILICA PARTICLES FOR USE IN THE SAME, AND KIT COMPRISING PLURAL KINDS OF THE SILICA PARTICLES IN COMBINATION

(75) Inventors: Hideki Aizawa, Tokyo (JP); Michio Ohkubo, Tokyo (JP); Michihiro Nakamura, Tokushima (JP); Hirokazu Miyoshi, Tokushima (JP)

(73) Assignees: The Furukawa Electric Co., Ltd., Tokyo (JP); The University of Tokushima, Tokushima-Shi (JP)

( * ) Notice: Subject to any disclaimer, the term of this patent is extended or adjusted under 35 U.S.C. 154(b) by 918 days.

(21) Appl. No.: 12/230,121

(22) Filed: Aug. 22, 2008

(65) Prior Publication Data
US 2009/0068639 A1 Mar. 12, 2009

Related U.S. Application Data

(63) Continuation of application No. PCT/JP2007/053227, filed on Feb. 21, 2007.

(30) Foreign Application Priority Data

Feb. 24, 2006 (JP) .................................. 2006-049303

(51) Int. Cl.
*G01N 33/543* (2006.01)
*G01N 33/53* (2006.01)

(52) U.S. Cl.
USPC ........... 436/523; 436/518; 436/524; 436/528; 436/546; 436/10; 436/56; 436/164; 436/171; 436/172; 435/6; 435/7.1; 435/287.2; 435/973; 422/73; 422/82.05; 422/82.08; 422/82.09

(58) Field of Classification Search
USPC ............ 435/6, 7.1, 287.2, 973; 436/518, 523, 436/524, 527, 528, 546, 10, 56, 164, 171, 436/172; 422/73, 82.05, 82.08, 82.09
See application file for complete search history.

(56) References Cited

U.S. PATENT DOCUMENTS 7,781,227 B2 * 8/2010 Mehrpouyan et al. ........ 436/523
2009/0017476 A1 * 1/2009 Tan et al. ..................... 435/7.32

FOREIGN PATENT DOCUMENTS

| JP | 04-127061 A | 4/1992 |
|---|---|---|
| JP | 04-363663 A | 12/1992 |
| JP | 05-72204 A | 3/1993 |
| JP | 2002-501184 A | 1/2002 |
| JP | 2002-537564 A | 11/2002 |
| JP | 2003-189893 A | 7/2003 |
| JP | 2004-533626 A | 11/2004 |
| JP | 2005-506547 A | 3/2005 |
| JP | 2005-535346 A | 11/2005 |
| WO | 03/036273 A1 | 5/2003 |
| WO | 2004/017041 A2 | 2/2004 |
| WO | 2004/073739 A1 | 9/2004 |
| WO | 2005/046449 A2 | 5/2005 |
| WO | 2005/100985 A2 | 10/2005 |

OTHER PUBLICATIONS

Yang et al., Nanometer fluorescent hybrid silica particles as ultrasensitive and photostable biological labels, Analyst 128: 462-466 (2003).*
Office Action dated Feb. 9, 2010 issued in corresponding Japanese application No. 2008-177409.
Varadan, P., Solomon, Michael J., Direct visualization of flow-induced microstructure in dense colloidal gels by confocal laser scanning microscopy, Department of Chemical Engineering, University of Michigan, Ann Arbor, Michigan (Received Oct. 1, 2002; final revision received Mar. 27, 2003), pp. 943-968.
Huang-Hao, Yang et al., Nanometer fluorescent hybrid silica particle as ultrasensitive and photostable biological labels, The Analyst, 2003, vol. 128, pp. 462-466.
Cook, E. B. et al., Simultaneous measurement of six cytokines in a single sample of human tears using microparticle-based flow cytometry: allergics vs. non-allergics; Journal of Immunological Methods 254 (2001), pp. 109-118.
Hooisweng OW et al.; Bright and Stable Core-Shell Fluorescent Silica Nanoparticles; Nano Letters; 2005; vol. 5; No. 1; pp. 113-117.
Japanese Office Action dated Jul. 13, 2010 issued in corresponding Japanese application No. 2008-177409 (with English translation.
Japanese Office Action dated Jul. 13, 2010 issued in corresponding Japanese application No. 2006-501743 (with English translation).
Japanese Office Action for Application No. 2008-117409, dated Dec. 7, 2010.
Japanese Office Action for Application No. 2008-501743, dated Nov. 9, 2010.

* cited by examiner

*Primary Examiner* — Gail R Gabel
(74) *Attorney, Agent, or Firm* — Birch, Stewart, Kolasch & Birch, LLP

(57) ABSTRACT

A system of quantitatively determining a biomolecule, which has: allowing fluorescent silica particles capable of emitting fluorescence detectable by a flow cytometer to capture a target biomolecule fluorescent-labelled for quantitative determination; detecting the fluorescence emitted from the fluorescent silica particles themselves by using the flow cytometer; and measuring the intensity of the fluorescence of the labelled target biomolecule, thereby quantitatively determining the target biomolecule.

15 Claims, 6 Drawing Sheets

SYSTEM AND METHOD OF QUANTITATIVELY DETERMINING A BIOMOLECULE, SYSTEM AND METHOD OF DETECTING AND SEPARATING A CELL BY FLOW CYTOMETRY, AND FLUORESCENT SILICA PARTICLES FOR USE IN THE SAME, AND KIT COMPRISING PLURAL KINDS OF THE SILICA PARTICLES IN COMBINATION

TECHNICAL FIELD

The present invention relates to a flow-cytometric assay system and an assay method by using fluorescent silica particles. Specifically, the present invention relates to a system and a method of quantitatively determining a biomolecule by flow cytometry with labelling of fluorescent silica particles, a system and a method of detecting and separating a cell by flow cytometry with labelling of fluorescent silica particles, and fluorescent silica particles different in properties that enables simultaneous detection by flow cytometry by using the system or the method mentioned above.

BACKGROUND ART

It is essential for early diagnosis of disease or accurate analysis of pathology, to determine quantitatively the amounts of biomolecules, such as cytokines, hormones, proteins and nucleic acids, contained in body fluids such as blood plasma, lymph and tissue fluid or to detect the trace amounts of biomolecules contained in the body fluids. An ELISA method, a chemoluminescence method or a bead assay by a flow cytometer is mainly practiced for quantitative determination or detection of biomolecules.

However, the ELISA and chemoluminescence methods, which detect only a single kind of biomolecule in a single reaction, unfavorably demanded an extended period and larger labor for detection of plural biomolecules and increase in cost, because the sample and the reagent are needed in greater amounts.

Bead assays by using a flow cytometer have been attracting attention recently as a method of quantitative determining plural kinds of biomolecules in a single operation (see e.g., Non-patent Document 1). The beads used in conventional bead assays are fluorescent-labelled polymer beads that have functional groups introduced onto the surface by surface treatment, which are additionally bound to biomolecules. Production of such beads demand sophisticated technique and tedious operation, making the beads very expensive.
[Non-patent Document 1] J. Immunological Methods 2001, 254, 109-118

DISCLOSURE OF INVENTION

For solving the above-mentioned problems, the present invention contemplates providing a system and a method of quantitatively determining a biomolecule and a system and a method of detecting and separating a cell, wherein fluorescent silica particles diversified in properties can be used as the capturing or labelling beads in flow cytometry, fluorescent silica particles for use therein, and a kit comprising plural kinds of the silica particles in combination.

According to the present invention, there is provided the following means:

(1) A system of quantitatively determining a biomolecule, comprising:

allowing fluorescent silica particles capable of emitting fluorescence detectable by a flow cytometer to capture a target biomolecule fluorescent-labelled for quantitative determination;

detecting the fluorescence emitted from the fluorescent silica particles themselves by using the flow cytometer; and measuring the intensity of the fluorescence of the labelled target biomolecule, thereby quantitatively determining the target biomolecule;

(2) The system of quantitatively determining a biomolecule described in (1), wherein two or more kinds of target biomolecules are specifically and respectively captured by two or more kinds of fluorescent silica particles, thereby quantitating the two or more kinds of target biomolecules simultaneously;

(3) The system of quantitatively determining a biomolecule described in (1) or (2), wherein the average diameter of the fluorescent silica particles is 300 nm or more;

(4) The system of quantitatively determining a biomolecule described in any one of (1) to (3), wherein the surface of the fluorescent silica particles is modified with a substance capable of specifically adsorbing or binding to the target biomolecule and the fluorescence emitted from the fluorescent silica particles themselves is resistant to photobleaching;

(5) The system of quantitatively determining a biomolecule described in (4), wherein the substance modifying the surface of the fluorescent silica particles and capable of specifically adsorbing or binding to the target biomolecule is further fluorescent-labelled;

(6) The system of quantitatively determining a biomolecule described in any one of (2) to (5), wherein the two or more kinds of fluorescent silica particles each contain one to four kinds of fluorescent dye compounds;

(7) The system of quantitatively determining a biomolecule described in any one of (2) to (6), wherein the two or more kinds of fluorescent silica particles have fluorescence intensities varying in plural phases, due to the content of the fluorescent dye compound varying in each particle;

(8) The system of quantitatively determining a biomolecule described in any one of (1) to (7), wherein the two or more kinds of fluorescent silica particles have different fluorescence spectra and/or different fluorescence intensities varying in plural phases;

(9) The system of quantitatively determining a biomolecule described in any one of (1) to (8), wherein the target biomolecule is an antigen, an antibody, a DNA, a RNA, a sugar, a polysaccharide, a ligand, a receptor, a peptide or a chemical substance;

(10) The system of quantitatively determining a biomolecule described in any one of (1) to (9), wherein the fluorescent silica particles may contain silica particles containing no fluorescent dye compound;

(11) The system of quantitatively determining a biomolecule described in any one of (1) to (10), wherein the silica particles are recognized by receiving the fluorescence of each of the silica particles;

(12) A method of quantitatively determining a biomolecule, comprising steps of:

immobilizing one or more kinds of target biomolecules labelled with fluorescence for quantitative determination on the surface of one or more kinds of fluorescent silica particles capable of emitting fluorescence detectable by using a flow cytometer and surface-modified with a substance capable of recognizing a target biomolecule molecularly;

detecting the fluorescence emitted respectively from the one or more kinds of fluorescent silica particles themselves; and quantitatively determining the intensity of the fluorescence from each of the one or more kinds of labelled target biomolecules by using the flow cytometer;

(13) A method of quantitatively determining a biomolecule, comprising steps of:

immobilizing one or more kinds of target biomolecules on the surface of one or more kinds of fluorescent silica particles capable of emitting fluorescence detectable by using a flow cytometer and surface-modified with a substance capable of recognizing a target biomolecule molecularly;

mixing one or more fluorescent-labelled probes capable of emitting fluorescence for quantitative determination and specifically binding to the one or more kinds of target biomolecules respectively;

detecting the fluorescence emitted respectively from the one or more kinds of fluorescent silica particles themselves; and quantitatively determining the intensity of the fluorescence from each of the one or more fluorescent-labelled probes by using the flow cytometer;

(14) A method of quantitatively determining a biomolecule, comprising steps of:

immobilizing one or more kinds of target biomolecules on the surface of one or more kinds of fluorescent silica particles capable of emitting fluorescence detectable by using a flow cytometer and surface-modified with a substance capable of recognizing a target biomolecule molecularly;

mixing one or more molecular recognition substances capable of specifically binding to the one or more kinds of target biomolecules respectively;

mixing one or more fluorescent-labelled probes capable of emitting fluorescence for quantitative determination and specifically binding to the one or more molecular recognition substances respectively;

detecting the fluorescence emitted respectively from the one or more kinds of fluorescent silica particles themselves; and quantitatively determining the intensity of the fluorescence from each of the one or more fluorescent-labelled probes by using the flow cytometer;

(15) The method of quantitatively determining a biomolecule described in (13) or (14), wherein the fluorescent-labelled probe is fluorescent silica particles surface-modified with a substance capable of specifically binding to the target biomolecule or the molecular recognition substance;

(16) The method of quantitatively determining a biomolecule described in any one of (13) to (15), wherein the target biomolecule is an antigen, an antibody, a DNA, a RNA, a sugar, a polysaccharide, a ligand, a receptor, a peptide or a chemical substance;

(17) The method of quantitatively determining a biomolecule according to any one of (12) to (16), wherein two or more kinds of target biomolecules are simultaneously quantitated;

(18) A system of detecting or separating a cell, having means of:

labelling one or more kinds of target cells in a sample solution by using one or more kinds of fluorescent silica particles capable of emitting fluorescence detectable by a flow cytometer;

detecting the fluorescence emitted from the fluorescent silica particles labelling the one or more kinds of target cells by using the flow cytometer; and separating the target cells as needed;

(19) The system of detecting or separating a cell, described in (18), wherein the surface of the fluorescent silica particles is modified with a substance capable of specifically adsorbing or binding to the surface marker of the target cell and the fluorescence emitted from the fluorescent silica particles is resistant to photobleaching;

(20) The system of detecting or separating a cell, described in (18), wherein the surface of the fluorescent silica particles is modified with a sugar-binding protein capable of specifically binding to the cortical sugar chain of the target cell and the fluorescence emitted from the fluorescent silica particles is resistant to photobleaching;

(21) The system of detecting or separating a cell, described in (18), wherein the surface of the fluorescent silica particles is modified with an antibody or a receptor capable of specifically binding to the surface antigen of the target cell and the fluorescence emitted from the fluorescent silica particles is resistant to photobleaching;

(22) The system of detecting or separating a cell, described in any one of (18) to (21), wherein the target cell is a myelocytic cell, a B lymphoid cell, a T lymphoid cell, a hematopoietic stem cell, a malignant tumor cell, a virus-infected cell or a heterologous graft cell;

(23) The system of detecting or separating a cell, described in any one of (18) to (22), wherein the average diameter of the fluorescent silica particles is 10 nm to 100 nm;

(24) The system of detecting or separating a cell, described in any one of (18) to (23), wherein two or more kinds of target cells are simultaneously detected or separated;

(25) A method of detecting or separating a cell, comprising steps of:

labelling one or more kinds of target cells in a sample solution by using one or more kinds of fluorescent silica particles capable of emitting fluorescence detectable by a flow cytometer;

detecting the fluorescence emitted from the fluorescent silica particles labelling the one or more kinds of target cells by using the flow cytometer; and separating the target cells as needed;

(26) The method of detecting or separating a cell, described in (25), wherein the surface of the fluorescent silica particles is modified with a substance capable of specifically adsorbing or binding to a surface marker of the target cell and the fluorescence emitted from the fluorescent silica particles is resistant to photobleaching;

(27) The method of detecting or separating a cell, described in (26), wherein the surface of the fluorescent silica particles is modified with a sugar-binding protein capable of specifically binding to a cortical sugar chain of the target cell and the fluorescence emitted from the fluorescent silica particles is resistant to photobleaching;

(28) The method of detecting or separating a cell, described in (18), wherein the surface of the fluorescent silica particles is modified with an antibody or a receptor capable of specifically binding to a surface antigen of the target cell and the fluorescence emitted from the fluorescent silica particles is resistant to photobleaching;

(29) The method of detecting or separating a cell, described in any one of (25) to (28), wherein the target cell is a myelocytic cell, a B lymphoid cell, a T lymphoid cell, a hematopoietic stem cell, a malignant tumor cell, a virus-infected cell or a heterologous graft cell;

(30) Fluorescent silica particles for labelling a target biomolecule for use as labelling beads resistant to photobleaching in flow cytometry, wherein a fluorescent dye compound and a silica component are bound to each other chemically or adsorbed on each other and the particles have an average diameter of 300 nm or more;

(31) Fluorescent silica particles for labelling a target cell for use as labelling beads resistant to photobleaching in flow cytometry, wherein a fluorescent dye compound and a silica component are bound to each other chemically or adsorbed on each other and the particles have an average diameter of 10 nm to 100 nm;

(32) A fluorescent material, which comprises the fluorescent silica particles described in (30) or (31);

(33) A multiplexing kit for flow cytometry, comprising at least a set of plural kinds of fluorescent silica particles described in (30) or (31) as labelling beads resistant to photobleaching;

(34) The multiplexing kit for flow cytometry described in (33), wherein the plural kinds of fluorescent silica particles may include silica particles containing no fluorescent dye compound;

(35) The multiplexing kit for flow cytometry described in (33) or (34), wherein the target biomolecule or the target cell is an antigen, an antibody, a DNA, a RNA, a sugar, a polysaccharide, a ligand, a receptor, a peptide, a chemical substance, a malignant tumor cell, a virus-infected cell or a heterologous graft cell;

(36) The multiplexing kit for flow cytometry described in any one of (33) to (35), wherein the surface of the fluorescent silica particles is modified with a substance capable of specifically adsorbing or binding to the target biomolecule and the fluorescence emitted from the fluorescent silica particles is resistant to photobleaching;

(37) The multiplexing kit for flow cytometry described in any one of (33) to (36), wherein the two or more kinds of fluorescent silica particles each contain one to four kinds of fluorescent dye compounds;

(38) The multiplexing kit for flow cytometry described in any one of (33) to (37), wherein the two or more kinds of fluorescent silica particles have fluorescence intensities varying in plural phases, due to the content of the fluorescent dye compound varying in each particle; and

(39) The multiplexing kit for flow cytometry described in any one of (33) to (38), wherein the two or more kinds of fluorescent silica particles have different fluorescence spectra and/or different fluorescence intensities varying in plural phases.

In the present invention, the term "fluorescence" has a broader meaning including phosphorescence. Thus in the present invention, the fluorescence lifetime is not particularly limited, and thus, the emission fluorescence lifetime may be $10^{-3}$ second to 1 day or more, preferably $10^{-10}$ second to $10^{-1}$ second, more preferably $10^{-9}$ second to $10^{-3}$ second, and still more preferably $10^{-9}$ second to $10^{-5}$ second.

The "fluorescence", which is light emission at the wavelength inherent to the fluorescent dye compound, is a phenomenon different from light absorption defined by the difference in light intensity between the incident light and the transmitted light from a light-absorbing substance. Accordingly, the light to be analyzed and also the measurement system such as analytical mechanism are different between fluorescence and light absorption.

Other and further features and advantages of the invention will appear more fully from the following description, appropriately referring to the accompanying drawings.

BEST MODE FOR CARRYING OUT THE INVENTION

Figure 1:
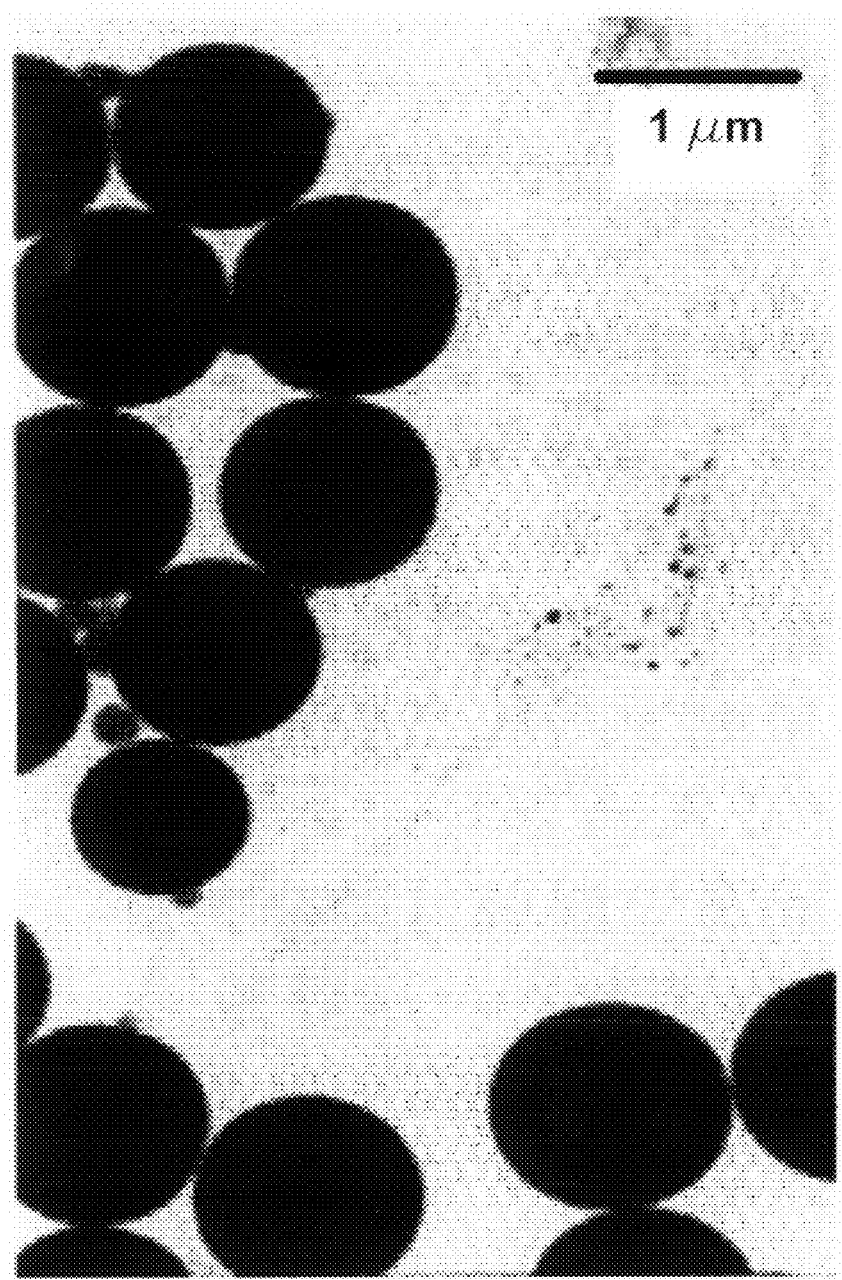
FIG. 1 is a TEM photograph showing the fluorescent silica particles obtained.

First, the "system of quantitatively determining a biomolecule of the present invention" will be described.

The system of quantitatively determining a biomolecule of the present invention comprises:

allowing fluorescent silica particles capable of emitting fluorescence detectable by a flow cytometer, as capturing- or labeling-beads resistant to photobleaching, to capture one or two or more kinds of target biomolecules (including a biologically active substance; the same shall apply hereinafter) fluorescent-labelled for quantitative determination;

detecting the fluorescence emitted from the fluorescent silica particles themselves by using the flow cytometer; and measuring the intensity of the fluorescence of the labelled target biomolecule, thereby quantitatively determining each of the target biomolecules.

The fluorescence for quantitative determination preferably has a fluorescence wavelength different from that emitted from the fluorescent silica particles themselves.

The system of the present invention allows quantitative determination of one or more kinds of target biomolecules simultaneously in a single flow-cytometric measurement operation. Particles and cells are detected by size (particle diameter) in conventional flow cytometry, but in the present invention, the kinds of target biomolecules can be quantitative determined, as the fluorescence of the fluorescent silica particles is detected by a flow cytometer.

Examples of the target biomolecule or the target bioactive substance include antigens, antibodies, DNAs, RNAs, sugars, polysaccharides, ligands, receptors, peptides, chemical substances and the like.

The fluorescent labelling for quantitative determination of the target biomolecule may be labelling of any fluorescent-labelled probe or labelling as a previously labelled target biomolecule, such as a nucleic acid (e.g., DNA or RNA) carrying a fluorescent dye compound such as Cy3 or Cy5 bound thereto by PCR reaction or a protein fused with a fluorescent protein.

The fluorescent-labelled probe is not particularly limited, if it adsorbs or binds to a target biomolecule specifically, and an example thereof includes an antibody having an arbitrary fluorescent dye compound bound thereto.

In the present description and claims, the term "ligand" means a substance capable of specifically binding to a protein, and examples thereof include substrates capable of binding to enzyme, coenzymes, regulatory factors, hormones, neurotransmitters, and the like, and thus, the ligands include low-molecular weight molecules as well as high-molecular weight substances.

The chemical substances include not only natural organic compounds but also bioactive compounds artificially prepared, environmental hormones, and the like.

Hereinafter, the flow cytometer for use in the present invention will be described.

The flow cytometer is an apparatus of supplying a particle suspension into a narrow tube, separating the suspended particles one by one, irradiating laser on each particle and detecting and measuring the fluorescence emission from the particle excited by the laser and the scattering of the laser by the particle. The flow cytometry is an analysis method using the same.

The flow cytometer for use in the present invention is not particularly limited, and any conventional flow cytometer may be used as it is. It has, for example, a laser source (e.g., He/Ne or argon) emitting a single-wavelength light in one or more detection regions. Laser sources emitting lights at different wavelengths may be installed in the different detection regions. The laser may be converged by using a beam-shaping lens.

Before irradiation with the laser, a sheath fluid (e.g., IsoFlow sheath fluid (trade name, manufactured by Beckmann Coulter), Dako Sheath Fluid (trade name, manufactured by Dako Japan, etc.)), and a sample solution containing a target biomolecule, fluorescent silica particles or the like are introduced into a flow cell, where the sheath fluids and the sample solution form laminar flow without mutual mixing. During flow in the flow cell, the sample solution flows, while forming a sample core as it is held between the sheath fluids, and is irradiated by laser when it passes through a laser irradiation zone.

The flow cytometer for use in the present invention can bring only a single fluorescent silica particle labeling the target biomolecule into the detection region under a particular flow condition and thus, allows acquisition of the detection data of the single fluorescent silica particle.

Thus, the flow cytometry is a so-called multiplexing system allowing simultaneously measurement of plural targets in a single measurement operation.

In the present invention, the flow rate during measurement is not particularly limited, but, for quantitative determination of the target biomolecule, a condition of 100 to 1,000 fluorescent silica particles/second may be used, and a condition of 100 to 1,000 cells/second may be used for detection or separation of the target cell.

For example, when FACS Calibur (trade name, manufactured by Becton, Dickinson and Company) is used as the flow cytometer, the difference between the sheath pressure (pressure of sheath fluid) and the sample pressure (pressure of sample solution) may be controlled to 1 to 2 kpsi.

It is possible to collect the fluorescence emitted from the fluorescent silica particles flowing in each detection region that are irradiated by laser through the detection region, by using one or more arbitrary fluorescence channels such as photomultiplier tubes (e.g., FL1, FL2 and FL3). The light reflected by the silica particle (forward scattering light or side scattering light) may be collected by using an arbitrary scattering light-condensing channel such as a photomultiplier tube.

The flow cytometer for use in the present invention preferably has data-accumulating and analyzing means (hardware or software) of recording and storing the data obtained by detection, by the fluorescence channel or the like, of the fluorescence emission or scattering light derived from each target biomolecule passing through the detection region.

The data-accumulating and analyzing means may be a commercially available product such as FACSDiVa, EXPO32, Summit, AppSan, Lysis II, or Cell Quest (all, trade names).

With the quantitative determination system or the quantitative determination method of the present invention, it is possible to recognize the silica particles only by detecting the fluorescence, when plural kinds of fluorescent silica particles different only in fluorescence are used in combination, i.e., when the plural silica particles are substantially uniform, particularly in particle diameter (so uniform that the difference is not detected only by the difference in scattering light).

Specifically, the quantitative determination system or the quantitative determination method of the present invention can has only a fluorescence-detecting region containing an irradiation laser for fluorescence emission and a fluorescence channel, while a scattering light-detecting region demanding tedious operation containing an irradiation laser for scattering light and the scattering light-condensing channel is eliminated. In this way, it is possible to reduce the size of the system and to make the method less tedious in operation.

On the other hand, the one or more kinds of fluorescent silica particles for use in the present invention may contain silica particles containing no fluorescent dye compound that do not emit fluorescence. In this case, the flow cytometer for use preferably has a scattering light-detecting region equipped with an irradiation laser for scattering light and a scattering light-condensing channel.

The flow cytometer for use in the present invention may be a commercially available flow cytometer such as FACS Calibur (trade name, manufactured by Becton, Dickinson and Company), PERFLOW Ana (trade name, manufactured by THE FURUKAWA ELECTRIC CO., LTD.), EPICS ALTRA (trade name, manufactured by Beckmann Coulter), CyAn (trade name, manufactured by Dako Japan), or JSAN (trade name, manufactured by Bay bioscience Co., Ltd.).

Hereinafter, the "fluorescent silica particles for use in the present invention" will be described.

The fluorescent silica particles for use in the present invention is a fluorescent material as fluorescent-labelled beads comprising a fluorescent dye compound and a silica component chemically bound to or adsorbed on each other that captures and labels a target biomolecule (including a biologically active substance).

In the present invention, the fluorescent dye compounds is immobilized in the fluorescent silica particles, the concentration of the fluorescent dye compound is preferably 75 mmol/L or less, and more preferably 5 to 60 mmol/L in the fluorescent silica particle.

The "concentration of the fluorescent dye compound in fluorescent silica particle" is a value calculated by dividing the molar number of the fluorescent dye compound by the volume of the fluorescent silica particle. The molar number of the fluorescent dye compound is determined from the light absorbance of the fluorescent silica particle-dispersed colloid, and the volume of the fluorescent silica particle is a value obtained by collecting, drying and weighing only the fluorescent silica particles and calculating by using a silica particle density of 2.3 g/cm$^3$.

The fluorescent silica particles for use in the present invention are preferably a fluorescent material wherein the fluorescent dye compound is distributed uniformly inside and on the surface of the fluorescent silica particles.

In the present invention, the phrase "a fluorescence is resistant to photobleaching" means that a degree of the decay in fluorescence intensity of the colloidal silica particles containing a fluorescent dye compound when a dispersion thereof is irradiated by an argon lamp for 30 minutes is 20% or less of that of the decay in fluorescence intensity of the fluorescent dye compound (for example, fluorescein) in a solution at the same concentration.

As described above, the flow cytometer can obtain detection data from each fluorescent silica particle that captures a target biomolecule and differentiate each fluorescent silica particle, and thus, use of bar-code labelling is preferable in the present invention. Accordingly, the fluorescent silica particles for use in the present invention are preferably a fluorescent material allowing bar-code labelling.

In the present invention, the "bar-code labelling" means labelling of a silica particle with various fluorescent characteristics.

In the present invention, the one or more kinds of fluorescent silica particles may contain silica particles containing no fluorescent dye compound.

In the present invention, each of the one or more kinds of fluorescent silica particles contains one to four kinds of fluorescent dye compounds different in fluorescent emission spectrum.

Examples thereof include: 5(6)-carboxyfluorescein and DY630-containing fluorescent silica particles prepared by the method described below of preparing the fluorescent silica particles for use in the present invention so as to contain 5(6)-carboxyfluorescein and DY630 as two kinds of fluorescent dye compounds; 5(6)-carboxyfluorescein and PerCP (Peridinin chlorophyll protein)-containing fluorescent silica particles prepared by a similar method; three-component 5(6)-carboxyfluorescein, PI (Propidium iodide) and DY635-containing fluorescent silica particles; and four-component 5(6)-carboxyfluorescein, PE (phycoerythrin), PerCP and DY635-containing fluorescent silica particles.

[Formula 1]

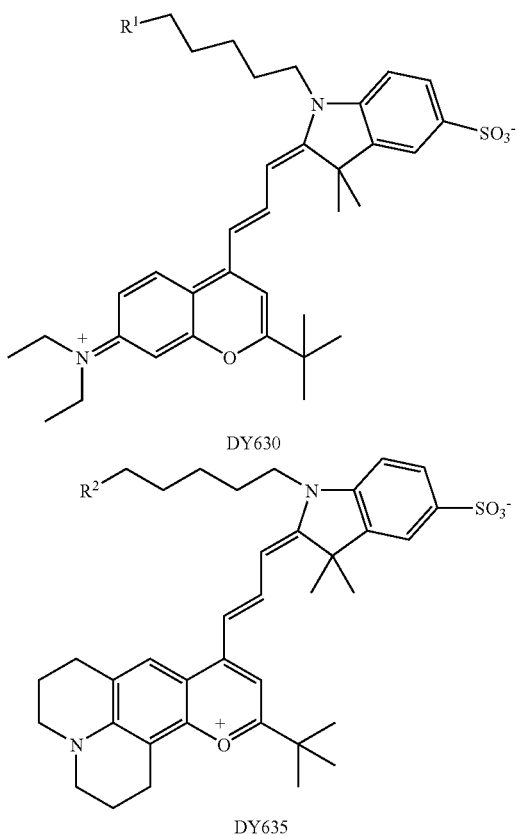

In the Formula, $R^1$ and $R^2$ each represent a group to covalently bond to the silica component.

Examples of the groups to covalently bond to the silica component include active ester groups such as NHS (N-hydroxysuccinimide) ester groups, maleimide group, isothiocyanate group, isocyanate group, cyano group, aldehyde group and the like.

Also, in the present invention, the one or more kinds of fluorescent silica particles preferably have fluorescence intensities varying in plural phases, due to the content of the fluorescent dye compound varying in each silica particle.

An example is plural kinds of fluorescent silica particles different in concentration of DY630 content because of the difference of the DY630 component (e.g., DY630-NHS ester) used in the silica particle preparation reaction, which are specifically prepared by the method described below of preparing the fluorescent silica particles containing DY630 for use in the present invention.

Specific examples of the plural kinds of DY630-containing silica particles include a combination of two kinds of silica particles: DY630-containing silica particles containing DY630 in the silica particle at a concentration of 53 mmol/L and DY630-containing silica particles containing DY630 in the silica particle at a concentration of 20 mmol/L; a combination of 5(6)-carboxyfluorescein-containing silica particles containing 5(6)-carboxyfluorescein in the silica particle at a concentration of 55 mmol/L and 5(6)-carboxyfluorescein-containing silica particles containing 5(6)-carboxyfluorescein in the silica particle at a concentration of 20 mmol/L.

More preferably in the present invention, each of the one or more kinds of fluorescent silica particles contains 1 to 4 kinds of fluorescent dye compounds different in fluorescence emission spectrum and have a fluorescence intensity in plural phases because of the difference in the content of the fluorescent dye compound contained in each silica particle.

For example, when two kinds of fluorescent dye compounds are used and the content of each fluorescent dye compound is varied independently in four phases for change in fluorescence intensity, there are 16 combinations obtained. In other words, it is possible to prepare a total of 16 kinds of fluorescent silica particles.

Typical examples thereof include the following 16 kinds of 5(6)-carboxyfluorescein and DY630-containing silica particles:

<1> nonfluorescent silica particles containing no dye,

<2> 5(6)-carboxyfluorescein-containing silica particles containing 5(6)-carboxyfluorescein in silica particle at a concentration of 8 mmol/L, <3> 5(6)-carboxyfluorescein-containing silica particles containing 5(6)-carboxyfluorescein in silica particle at a concentration of 20 mmol/L, <4> 5(6)-carboxyfluorescein-containing silica particles containing 5(6)-carboxyfluorescein in silica particle at a concentration of 60 mmol/L, <5> DY630-containing silica particles containing DY630 in silica particle at a concentration of 8 mmol/L, <6> 5(6)-carboxyfluorescein and DY630-containing silica particles containing 5(6)-carboxyfluorescein at a concentration of 8 mmol/L and DY630 at a concentration of 8 mmol/L in silica particle, <7> 5(6)-carboxyfluorescein and DY630-containing silica particles containing 5(6)-carboxyfluorescein at a concentration of 20 mmol/L and DY630 at a concentration of 8 mmol/L in silica particle, <8> 5(6)-carboxyfluorescein and DY630-containing silica particles containing 5(6)-carboxyfluorescein at a concentration of 60 mmol/L and DY630 at a concentration of 8 mmol/L in silica particle, <9> 5(6)-DY630-containing silica particles containing DY630 at a concentration of 20 mmol/L, <10> 5(6)-carboxyfluorescein and DY630-containing silica particles containing 5(6)-carboxyfluorescein at a concentration of 8 mmol/L and DY630 at a concentration of 20 mmol/L in silica particle, <11> 5(6)-carboxyfluorescein and DY630-containing silica particles containing 5(6)-carboxyfluorescein at a concentration of 20 mmol/L and DY630 at a concentration of 20 mmol/L in silica particle, <12> 5(6)-carboxyfluorescein and DY630-containing silica particles containing 5(6)-carboxyfluorescein at a concentration of 60 mmol/L and DY630 at a concentration of 20 mmol/L in silica particle, <13> 5(6)-carboxyfluorescein and DY630-containing silica particles containing 5(6)-carboxyfluorescein at a concentration of 8 mmol/L and DY630 at a concentration of 60 mmol/L in silica particle, <14> DY630-containing silica particles containing DY630 at a concentration of 60 mmol/L, <15> 5(6)-carboxyfluorescein and DY630-containing silica particles containing 5(6)-carboxyfluorescein at a concentration of 20 mmol/L and DY630 at a concentration of 60 mmol/L in silica particle, and <16> 5(6)-carboxyfluorescein and DY630-containing silica particles containing 5(6)-carboxyfluorescein at a concentration of 60 mmol/L and DY630 at a concentration of 60 mmol/L in silica particle.

In the present invention, some of the 16 kinds of silica particles may be used in combination.

The fluorescent silica particles for use in the present invention are preferably those modified with a substance capable of specifically adsorbing or binding to a target biomolecule for quantitative determination contained in a sample (e.g., arbitrary cell extract, lysate, medium-culture solution, solution, buffer), more preferably those modified with a substance capable of recognizing the target biomolecule molecularly.

Also in the present invention, silica particles different variously in fluorescence characteristics may be prepared by using an fluorescent-labelled substance as the substance capable of specifically adsorbing or binding to the target biomolecule for quantitative determination contained in the sample.

The fluorescence preferably has a wavelength different from that of the fluorescent of silica particles above or that for quantitative determination.

Examples of such silica particles include the following four kinds of DY630-containing silica particles:

<1> DY630-containing silica particles containing DY630 at a concentration of 53 mmol/L in silica particle and having a fluorescein-labelled substance capable of specifically adsorbing or binding to the target biomolecule;

<2> DY630-containing silica particles containing DY630 at a concentration of 53 mmol/L in silica particle and having a fluorescent-unlabelled substance capable of specifically adsorbing or binding to the target biomolecule;

<3> DY630-containing silica particles containing DY630 at a concentration of 20 mmol/L in silica particle and having a fluorescein-labelled substance capable of specifically adsorbing or binding to the target biomolecule; and <4> DY630-containing silica particles containing DY630 at a concentration of 20 mmol/L in silica particle and having a fluorescent-unlabelled substance capable of specifically adsorbing or binding to the target biomolecule.

The method of modifying the surface of the fluorescent silica particles for use in the present invention by binding of a substance capable of molecularly recognizing the target biomolecule will be described below, separately in the section of "surface modification of silica particles".

Examples of the substances capable of molecularly recognizing the target biomolecule with which the fluorescent silica particles are modified include antibodies, antigens, peptides, DNAs, RNAs, polysaccharides, receptors and the like.

The substance capable of molecularly recognizing the target biomolecule that modifies the fluorescent silica particles can bind, as a receptor, to the target biomolecule specifically in specific molecular recognition, such as, antigen-antibody reaction, biotin-avidin reaction or hybridization by using the complementarity of nucleotide sequences.

The "adsorption" above is binding by Van der Waals force, hydrophobic interaction, or electrostatic interaction.

Herein, the "molecular recognition" means a specific interaction between biomolecules (including bioactive substances) such as (1) hybridization between DNA's, between a DNA and a RNA, or between RNA's, (2) antigen-antibody reaction, or (3) enzyme (receptor)-substrate (ligand) reaction. And the site of specific interaction is called a recognition site.

Hereinafter, the fluorescent dye compound for use in the present invention will be described.

As described above, the fluorescent dye compound for use in the present invention is a fluorescent dye compound in the broader sense, and may comprise a phosphorescent dye compound.

The fluorescent dye compound is not particularly limited, but preferably a fluorescent dye compound having the excitation wavelength at which the compound used in flow cytometry is excited by laser.

Examples of the fluorescent dye compounds excited at the argon laser excitation wavelength of 488 nm include 5(6)-carboxyfluorescein, PE (phycoerythrin, manufactured by Invitrogen), PE-Cy5 and PE-Cy7 (trade names, manufactured by Amersham Biosciences), DY495 and DY505 (trade names, manufactured by Dyomics GmbH), BODIPY-TAMRA-X (trade name, manufactured by Invitrogen), and the like.

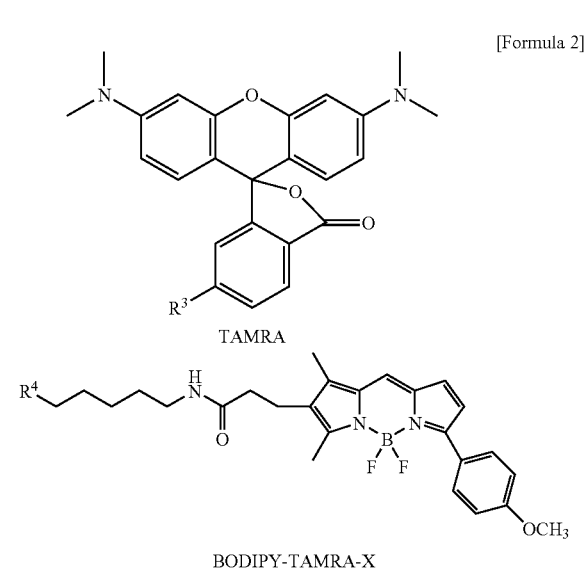

[Formula 2]

TAMRA

BODIPY-TAMRA-X

In the Formula, $R^3$ and $R^4$ each represent a group to covalently bond to the silica component.

Fluorescent dye compounds having the YAG laser excitation wavelength of 532 nm include 5-TAMRA and Cy3 (trade names, manufactured by Amersham Biosciences), DY550 and DY555 (trade names, manufactured by Dyomics GmbH), Alexa Fluor546 and Alexa Fluor555 (trade names, manufactured by Invitrogen) and the like.

Fluorescent dye compounds having the semiconductor red laser excitation wavelength of 635 nm include DY630, DY631, DY633, DY635, DY636, DY650 and DY651 (trade names, manufactured by Dyomics GmbH), Cy5 (trade name, manufactured by Amersham Biosciences), BODIPY 630/650, Alexa Fluor633, Alexa Fluor647 and APC (allophycocyanin) (trade names, manufactured by Invitrogen), Oyster643 and Oyster656 (trade names, manufactured by Denovo Biolabels) and the like.

[Formula 3]

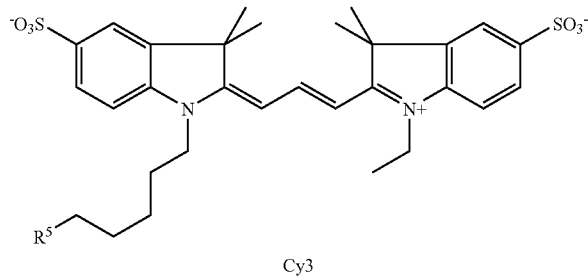

Cy3

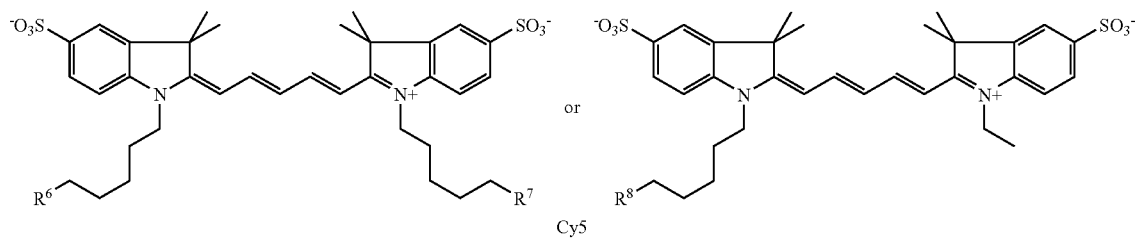

Cy5

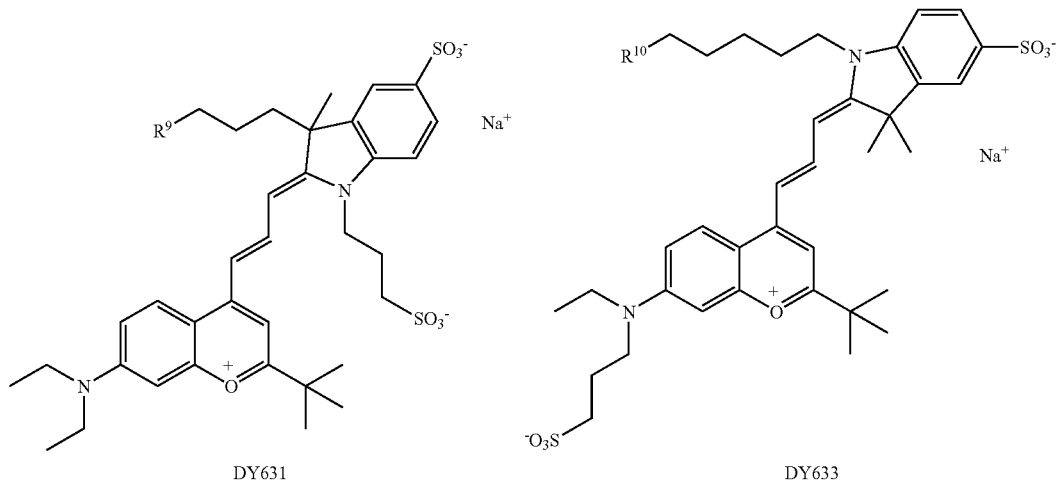

DY631       DY633

[Formula 4]

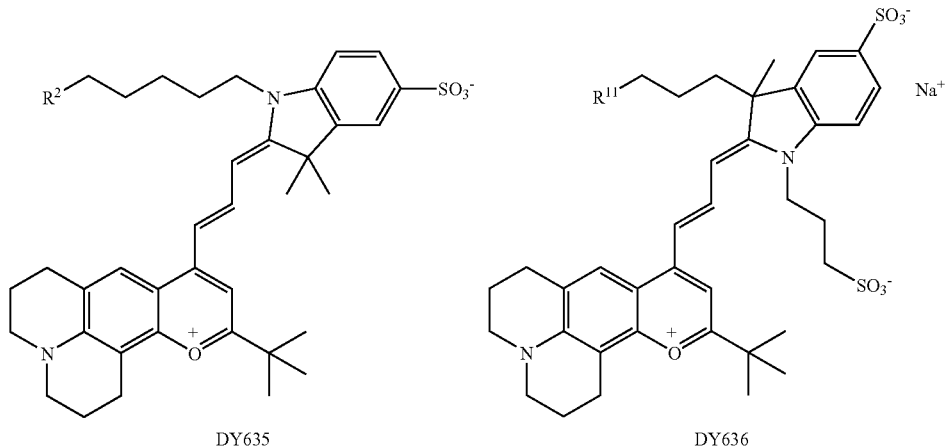

DY635       DY636

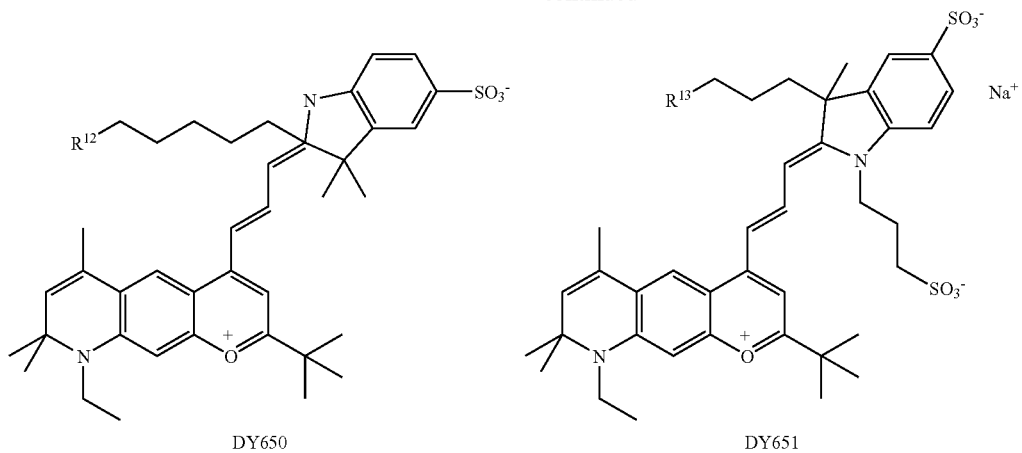

DY650  DY651

In the Formulae, $R^5$, $R^6$, $R^7$, $R^8$, $R^2$, $R^9$, $R^{10}$, $R^{11}$, $R^{12}$ and $R^{13}$ each represent a group to covalently bond to the silica component.

Hereinafter, a method of preparing the fluorescent silica particles for used in the present invention will be described.

The fluorescent silica particles used in the present invention can be prepared by allowing a fluorescent dye compound to react with a silane compound, thereby forming a chemical, covalent or ionic bond to, or to be adsorbed on the silane compound and further polymerizing one or more silane compounds with the product thus obtained.

The fluorescent silica particles are preferably prepared by allowing a fluorescent dye compound having an active group such as N-hydroxysuccinimide (NHS) ester group, maleimide group, isocyanate group, isothiocyanate group, aldehyde group, para-nitrophenyl group, diethoxymethyl group, epoxy group, or cyano group, to react with a silane-coupling agent having a substituent group reactive with the active group (such as amino group, hydroxyl group, or thiol group), forming a covalent bond and additionally polymerizing one or more silane compounds with the product thus obtained.

The inventors have earlier filed patent applications on a method of preparing fluorescent silica particles (e.g., Japanese Patent Application No. 2004-356608).

The fluorescent silica particles are more preferably prepared according to the method. Specifically, the fluorescent silica particles can be prepared in the following steps (a) and (b):

a step (a) of forming a dye/silane-coupling agent composite compound (3) in reaction of a fluorescent dye compound (1) containing an active ester group such as N-hydroxysuccinimide (NHS) ester with an amino group-containing silane-coupling agent (2), and a step (b) of polymerizing a silica compound (4) with the dye/silane-coupling agent composite compound (3) obtained in the step (a) under a basic condition to form the fluorescent silica particle (5).

The inventors have filed patent applications on the step of esterifying a carboxylic acid compound with N-hydroxysuccinimide (for example, Japanese Patent Application No. 2004-356608).

The NHS ester group-containing fluorescent dye compound (1) used in the step (a) may be prepared according to the esterification reaction step therein. However, a commercially available product may be used instead.

Specific examples of the NHS ester group-containing fluorescent dye compounds (1) include 5(6)-carboxyfluorescein-NHS ester (trade name, manufactured by Roche), DY550-NHS ester, DY555-NHS ester, DY630-NHS ester and DY635-NHS ester (trade names, manufactured by Dyomics GmbH), 5-TAMRA-NHS ester, Alexa Fluor546-NHS ester, Alexa Fluor555-NHS ester, Alexa Fluor633-NHS ester, Alexa Fluor647-NHS ester (trade names, manufactured by Invitrogen), Oyster643-NHS ester, Oyster656-NHS ester (trade names, manufactured by Denovo Biolabels), and the like. Among them, 5(6)-carboxyfluorescein-NHS ester (trade name, manufactured by Roche) and DY630-NHS ester are preferable.

The amino group-containing silane-coupling agent (2) is not particularly limited, and examples thereof include γ-aminopropyltriethoxysilane (APS), 3-[2-(2-aminoethylamino)ethylamino]propyltriethoxysilane, N-2-(aminoethyl)-3-aminopropylmethyldimethoxysilane, and 3-aminopropyltrimethoxysilane. Among them, APS is preferable.

The reaction between the NHS ester group-containing fluorescent dye compound (1) and the amino group-containing silane-coupling agent (2) may be carried out, by dissolving the ingredients in a solvent such as DMSO or water and reacting the mixture while stirring at room temperature (for example, 25° C.).

The ratio of the NHS ester group-containing fluorescent dye compound (1) to the silane-coupling agent (2) used in the reaction is not particularly limited, but the ratio of the NHS ester group-containing fluorescent dye compound (1) to the amino group-containing silane-coupling agent (2) is preferably 1:0.5 to 4 (molar ratio), more preferably 1:0.8 to 1.2 (molar ratio).

Thus, a dye/silane-coupling agent composite compound (3) can be obtained by reacting the carbonyl group in the fluorescent dye compound (1) with the amino group of the amino group-containing silane-coupling agent (2), thereby forming an amide bond (—NHCO—). In other words, a fluorescent dye compound and a silica component are bound to each other via an amide bond in the dye/silane-coupling agent composite compound (3).

In the subsequent step (b), the dye/silane-coupling agent composite compound (3) is allowed to react with a silica compound (4). The silica compound (4) is not particularly limited, and examples thereof include tetraethoxysilane (TEOS), γ-mercaptopropyltrimethoxysilane (MPS), γ-mercaptopropyltriethoxysilane, γ-aminopropyltriethoxysilane (APS), 3-thiocyanatopropyltriethoxysilane, 3-glycidyloxypropyltriethoxysilane, 3-isocyanatopropyltriethoxysilane, and 3-[2-(2-aminoethylamino)ethylamino]propyltriethoxysilane. Among them, TEOS, MPS, and APS are preferable.

The ratio of the dye/silane-coupling agent composite compound (3) to the silica compound (4) is not particularly limited, but the molar ratio of the silica compound (4) to one mole of the dye/silane-coupling agent composite compound (3) is preferably 50 to 40,000, more preferably 100 to 2,000, and still more preferably 150 to 1,000.

The reaction is preferably carried out in the presence of alcohol, water, and ammonia. The alcohol is, for example, a lower alcohol having 1 to 3 carbon atoms such as methanol, ethanol, or propanol.

The ratio of water to alcohol in the reaction system is not particularly limited, but, the alcohol is used in an amount in the range of 0.5 to 20 parts, more preferably 2 to 16 parts, and still more preferably 4 to 10 parts by volume, with respect to one part of water by volume. The amount of ammonia is not particularly limited, but the ammonia concentration is preferably 30 to 1,000 mM, more preferably 60 to 500 mM, and still more preferably 80 to 200 mM.

The reaction may be carried out at room temperature, preferably as it is stirred. Generally, the fluorescent silica particles (5) can be prepared in a reaction period of several dozen minutes to several dozen hours.

It is possible to control the size (diameter) of the silica particles to be prepared properly by adjusting the concentration of the silica compound (4) used and the reaction time in the step (b). It is also possible to prepare larger silica particles by increasing the concentration of the silica compound (4) used and elongating the reaction time (see, for example, Blaaderen et al., "Synthesis and Characterization of Monodisperse Colloidal Organo-silica Spheres", J. Colloid and Interface Science 156, 1-18. 1993). Further, it is possible to prepare larger silica particles by repeating the step (b) plural times. It is thus possible to adjust the particle diameter of the fluorescent silica particles obtained freely in a desirable range, for example, in the order of from nm order to μm. It is also possible as needed to make the particles have a desirable particle diameter distribution by an additional treatment, and thus to produce silica particle having a particle diameter distribution in a desirable range.

The fluorescent silica particles thus obtained may be purified as needed by a usual method, for example by using an ultrafiltration membrane, for removal of copresent ions and impurities.

Spherical or almost spherical silica particles can be prepared by the method described above. Specifically, the almost spherical particles mean particles having a major axis/minor axis ratio of 2 or less.

In the system or the method of quantitatively determining a biomolecule of the present invention, the average diameter of the fluorescent silica particles is preferably 300 nm or more, more preferably 500 nm or more, still more preferably 800 nm or more, and particularly preferably 800 nm to 1200 nm, from the viewpoint of the detection efficiency (sensitivity) in a flow cytometer.

On the other hand, in the system or the method of detecting or separating a cell of the present invention, the average diameter of the fluorescent silica particles is preferably 10 nm or more, more preferably 10 nm to 200 nm, still more preferably 10 nm to 100 nm, and particularly preferably 10 nm to 50 nm, for improvement of cell detection sensitivity.

For obtaining silica particles having a desirable average diameter, it is possible to remove particles having a smaller particle diameter by ultrafiltration by using an ultrafiltration film such as YM-10 or YM-100 (trade name, manufactured by Millipore Corporation).

In the present invention, the average diameter is an average diameter of the circle (average circle-equivalent diameter) obtained by measuring the total projected area of 50 randomly-selected silica particles for example in an image obtained under transmission electron microscope (TEM) or scanning electron microscope (SEM) using an image processing equipment, dividing the total area with the number of the silica particles (50), and determining the circle having an area equivalent to that.

The variation coefficient, so-called CV value, of the particle size distribution is not particularly limited, but preferably 10% or less, more preferably 8% or less.

In the present description and the claims thereof, a term "monodispersion" is used for particles having a CV value of 15% or less.

When immobilized and embedded in the silica particle, a plurality of the fluorescent dye compounds are dispersed inside the silica particle and thus, become more sensitive than its free fluorescent dye compound.

In addition, the inventors found that the silica particles allows immobilization and embedding of a plurality of fluorescent dye compounds therein without self-quenching (see, for example, Japanese Patent Application No. 2004-356608). For that reason, it gives a high-sensitivity labelled product that can be used even in minute regions.

Hereinafter, "surface modification of the silica particle" will be described.

Generally, silica is known to be inactive chemically and easily modified. Any desirable substance can also be bound to the surface of the fluorescent silica particles used in the present invention easily. Further, the surface of the fluorescent silica particle can be made the surface mesoporous or smooth.

Specifically according to the kind of the silica compound (4) used in the step (b), the fluorescent silica particle used in the present invention can be surface-modified to fluorescent silica particles having, on the surface, an acceptor group that can bind to a desirable substance. The acceptor group is, for example, an amino, a hydroxyl, a thiol, a carboxyl, a maleimide, or a succinimidyl ester group.

The relationship between the silica compound (4) used in reaction and the acceptor group formed on the surface of the fluorescent silica particles thus obtained are shown in Table 1.

TABLE 1

| Silica compound (4) | Acceptor group formed on silica particle surface |
|---|---|
| Tetraethoxysilane | OH group |
| γ-Mercaptopropyltriethoxysilane | SH group |
| Aminopropyltriethoxysilane | $NH_2$ group |
| 3-Thiocyanato propyl triethoxysilane | SCN group |
| 3-Glycidyloxypropyltriethoxysilane | Epoxy group |
| 3-Isocyanato propyl triethoxysilane | CNO group |

If an acceptor group different from the acceptor group introduced on the surface of each of the fluorescent silica particles obtained above (5) with the silica compound (4) used in the reaction is to be introduced, the fluorescent silica particles (5) are treated additionally with a silica compound different from the silica compound (4) used in step (b). The treatment can be performed by an operation similar to that in step (b), by using a silica compound different from the silica compound (4) used in step (b).

The fluorescent silica particles used in the present invention allows binding to or adsorption on the surface and modification of a desirable substance [such as antigen, antibody, DNA, RNA, sugar, polysaccharide, ligand, receptor, peptide, chemical substance, or the like] capable of recognizing the target biomolecule molecularly, according to the kind of the acceptor group present on the surface.

The method of binding and modifying the surface of the fluorescent silica particles used in the present invention with the substance capable of recognizing the target biomolecule molecularly is not particularly limited, and examples thereof include the following methods (i) to (iii).

(i) Fluorescent silica particles having thiol groups on the surface such as those prepared by using MPS or the like can be modified on the surface with the substance molecularly capable of recognizing the target biomolecule via a disulfide bond, a thioester bond, or a bond formed by thiol substitution reaction.

(ii) In particular when the substance capable of recognizing the target biomolecule molecularly has amino group, the thiol group on the fluorescent silica particles and the amino group on the substance capable of recognizing the target biomolecule molecularly may be bound to each other, by using a crosslinking agent such as succinimidyl-trans-4-(N-maleimidylmethyl)cyclohexane-1-carboxylate (SMCC) or N-(6-maleimidocaproyloxy)succinimide (EMCS).

(iii) In the case of fluorescent silica particles which have amino groups on the surface such as those prepared by using APS or the like, the amino group thereof and the thiol group of the substance capable of recognizing the target biomolecule molecularly may be bound to each other by using a crosslinking agent such as SMCC or EMCS, as described above. Alternatively, the amino group on the particle and the amino group of the substance capable of recognizing the target biomolecule molecularly may be bound to each other by using a crosslinking agent such as glutaric aldehyde or the like. Yet alternatively, the surface may be modified with the substance capable of recognizing the target biomolecule molecularly via an amide bond or a thiourea bond.

In the present invention, it is possible, for example, to concentrate a molecule present even at low concentration as diffused in a solution, by binding it onto the surface of the fluorescent silica particle and thus, to detect the molecule at high sensitivity.

Hereinafter, the "multiplexing kits for flow cytometry" will be described.

The multiplexing kit for flow cytometry can be prepared as capturing- or labeling-beads resistant to photobleaching (preferably, as bar-code labelling beads) in combination of two or more kinds of fluorescent silica particles for use in the present invention different in the fluorescence characteristics.

In the scope of the present description and the claims, the "multiplexing" means simultaneous analysis (detection, quantitative determination, etc.) of plural kinds of targets (biomolecules, cells, etc.) in a single measurement operation.

The multiplexing kit for flow cytometry of the present invention preferably comprises a combination of plural kinds of fluorescent silica particles surface-modified so as to respectively recognize different targets (biomolecules, cells, etc.) molecularly, in viewpoint of immediately applying the kit to flow cytometry.

The plural kinds of modified fluorescent silica particles are prepared by the method described in the section of "surface modification of silica particles".

Hereinafter, the "method of determining a target biomolecule quantitatively" will be described.

Examples of the target biomolecule used in the quantitative determination method of the present invention include antigens, antibodies, DNAs, RNAs, sugars, polysaccharides, ligands, receptors, peptides, chemical substances and the like.

Examples of the methods of quantitatively determining a biomolecule of the present invention include the following first to third embodiments:

The first embodiment of the method of quantitatively determining a biomolecule of the present invention comprises steps of:

immobilizing one or more kinds of target biomolecules labelled with fluorescence for quantitative determination on the surface of one or more kinds of fluorescent silica particles capable of emitting fluorescence detectable by a flow cytometer and surface-modified with a substance capable of recognizing a target biomolecule molecularly; and detecting the fluorescence emitted respectively from the one or more kinds of fluorescent silica particles themselves; and quantitatively determining the intensity of the fluorescence from each of the one or more kinds of labelled target biomolecules by using a flow cytometer.

The first embodiment is used preferably when the target biomolecule is previously labelled with fluorescence for quantitative determination. Accordingly, it is a method of:

immobilizing the target biomolecule on the surface of fluorescent silica particles with a fluorescent silica particles surface-modified with a substance capable of recognizing the target biomolecule molecularly;

detecting the fluorescence of the one or more kinds of fluorescent silica particles respectively by measuring the particles by using a flow cytometer, dividing the data obtained according to the kinds of the fluorescent silica particles; and thus, determining the amount of the target biomolecule from the intensity of the fluorescence for quantitative determination of the target biomolecule.

The target biomolecule in the first embodiment is, for example, a nucleic acid, such as DNA or RNA, having Cy3 or Cy5 introduced by PCR reaction, a protein fused with a fluorescent protein, or the like.

The one or more kinds of fluorescent silica particles surface-modified with the substance capable of recognizing the target biomolecule molecularly for use as labelling beads resistant to photobleaching (preferably, bar-code labelling beads) in the first to third embodiments of the method of quantitatively determining a biomolecule of the present invention are already described in the sections of "fluorescent silica particles for use in the present invention" and "surface modification of silica particles".

The second embodiment of the method of quantitatively determining a biomolecule of the present invention comprises steps of:

immobilizing one or more kinds of target biomolecules on the surface of one or more kinds of fluorescent silica particles capable of emitting fluorescence detectable by a flow cytometer and surface-modified with a substance capable of recognizing the target biomolecule molecularly;

mixing one or more kinds of fluorescent-labelled probes capable of emitting fluorescence for quantitative determination and respectively binding to the one or more kinds of target biomolecules specifically; and detecting the fluorescence emitted from the one or more kinds of fluorescent silica particles themselves respectively; and quantitatively determining the intensity of the fluorescence from each of the one or more fluorescent-labelled probes by using a flow cytometer.

The second embodiment is used preferably when the one or more kinds of target biomolecules have respectively two or more recognition sites (epitopes, or the like). Accordingly, it is a method of:

immobilizing the target biomolecule on the surface of fluorescent silica particles with fluorescent silica particles surface-modified with a substance capable of recognizing one recognition site of the target biomolecule molecularly;

labelling another recognition site of the target biomolecule for quantitative determination with a fluorescent-labelled probe for quantitative determination, measuring the particles by using a flow cytometer, detecting the fluorescence of the one or more kinds of fluorescent silica particles, dividing the data according to the kinds of the fluorescent silica particles, and thus;

determining the amount of the target biomolecule quantitatively from the intensity of the fluorescence from the fluorescent labelled probe.

Typical examples of the target biomolecules having two or more recognition sites in the molecule include any antigens (IL-2, IL-4, IL-5, IL-10, TNF-α, IFN-γ, erythropoietin, hematopoietic stem cell factor, transforming growth factors α and β, nerve cell growth factor, etc.), nucleic acids (DNAs and RNAs), antibodies (immunoglobulin A, immunoglobulin E, immunoglobulin G, and immunoglobulin M), and the like.

As long as the fluorescent-labelled probe contains a fluorescent material emitting a fluorescence at a wavelength different from that of the silica particles used and binds or adsorbs to the target biomolecule specifically, the fluorescent-labelled probe is not particularly limited. Examples thereof include any antibody bound to a fluorescent dye. The fluorescent-labelled probe may be fluorescent silica particles modified with a substance specifically binding to the target biomolecule or the molecular recognition substance.

Examples of the fluorescent-labelled probe include PE (phycoerythrin)-labelled anti-IL-2 antibody, PE-labelled anti-IL-4 antibody, PE-labelled anti-IL-5 antibody, PE-labelled anti-IL-10 antibody, PE-labelled anti-TNF-α antibody, PE-labelled anti-IFN-γ antibody, PE-labelled anti-erythropoietin antibody, PE-labelled anti-hematopoietic stem cell factor antibody, PE-labelled anti-transforming growth factor α antibody, PE-labelled anti-transforming growth factor β antibody, PE-labelled anti-nerve cell growth factor antibody and the like.

The third embodiment of the method of quantitatively determining a biomolecule of the present invention comprises steps of:

immobilizing one or more kinds of target biomolecules on the surface of one or more kinds of fluorescent silica particles capable of emitting fluorescence detectable by a flow cytometer and surface-modified with a substance capable of recognizing the target biomolecule molecularly;

mixing one or more kinds of molecular recognition substances capable of respectively binding to the one or more kinds of target biomolecules specifically;

mixing one or more kinds of fluorescent-labelled probes capable of emitting fluorescence for quantitative determination and respectively binding to or adsorbing the one or more kinds of molecular recognition substances specifically; and detecting the fluorescence emitted from the one or more kinds of fluorescent silica particles themselves respectively and quantitatively determining the amounts of the one or more fluorescent-labelled probes from each of the intensity of the fluorescence, by using a flow cytometer.

In the third embodiment, the molecular recognition substance is not particularly limited, as long as it binds to or adsorbs to the target biomolecule specifically, and is preferably a substance capable of recognizing the target biomolecule molecularly, and typical examples thereof include antigens, antibodies (preferably, any primary antibodies), DNAs, RNAs, saccharides, sugar chains, ligands, receptors, peptides and/or chemical substances.

The molecular recognition substance is, for example, a substance modified to recognize the target biomolecule, and examples thereof include biotin- or avidin-modified DNAs and RNAs, biotin- or avidin-modified mouse IgG, maltose-binding protein-modified mouse IgM, and the like.

The method of preparing the molecular recognition substances modified to recognize the target biomolecule is described in, for example, JP-A-9-154599 ("JP-A" means unexamined published Japanese patent application) and JP-T-2003-522158 ("JP-T" means searched and published International patent application) and the like.

The fluorescent-labelled probe for quantitative determination in the third embodiment is not particularly limited, as long as it has a fluorescence label and binds to or adsorbs to the molecular recognition substance specifically, and, it is, for example, an avidin- or streptoavidin-bound fluorescent-labelled probe when the molecular recognition substance is a biotinated antibody, and a biotin-bound fluorescent-labelled probe when the molecular recognition substance is an avidinated or streptoavidinated antibody. In addition, if the molecular recognition substance is a primary antibody, the fluorescent-labelled probe may be a fluorescent-labelled secondary antibody. The secondary antibody is not particularly limited, as long as it has an affinity to the primary antibody, and any antibody may be used.

Hereinafter, the system of detecting or separating a target cell and the method of detecting or separating a target cell (hereinafter, referred to simply as "the system and the method of detecting or separating a target cell of the present invention") in another embodiment of the present invention will be described.

The system and the method of detecting or separating a target cell of the present invention comprises: labelling one or more kinds of target cells in sample by using one or more kinds of fluorescent silica particles capable of emitting fluorescence detectable by a flow cytometer as labeling-bead resistant to photobleaching; and detecting the fluorescence emitted from the fluorescent silica particles labeling the one or more kinds of target cells by using the flow cytometer.

The target cell is not particularly limited, but examples thereof include myelocytic cell, B lymphoid cell, T lymphoid cell, hematopoietic stem cell, malignant tumor cell (e.g., HeLa cell), virus-infected cell (e.g., influenza virus-infected cell), heterologous graft cell (e.g., porcine liver cell), and the like.

In the system and the method of detecting or separating a target cell of the present invention, the surface of the fluorescent silica particles is preferably modified with a substance capable of specifically adsorbing or binding to the target cell surface marker.

If the target cell has cortical sugar chain (e.g., maltose in any cellular cortical sugar chain, sialyl Lewis X-containing sugar chain in any cellular surface layer) as the surface marker, the surface of the fluorescent silica particles is preferably modified with an antibody or a receptor capable of specifically binding to the target cell cortical sugar chain (e.g., maltose-binding protein, any sialyl Lewis X-recognizing selectin).

If the target cell has a surface antigen (e.g., porcine liver cell cortical α-Gal epitope) as the surface marker, the surface of the fluorescent silica particles is preferably modified with an antibody (e.g., human anti-α-Gal antibody) or a receptor capable of specifically binding to the target cell surface antigen.

In the system and the method of detecting or separating a target cell of the present invention, an arbitrary cell sorter is preferably installed in the flow cytometer used for separation of the target cell. The cell sorter may be any device, for example by water-droplet charging method or cell capture method.

The cell sorter is, for example, is a device of obtaining detection data on each fluorescent silica particles by laser irradiation in a flow cytometer as described above, electrically charging the sample core positively or negatively based on the acquired data, and sorting the sample core by using a voltage plate.

In the present invention, a commercially available cell sorter, such as MoFlo (trade name; manufactured by Dako Japan), may be used, or alternatively, a flow cytometer equipped with a commercially available cell sorter, such as PERFlow All (trade name, manufactured by THE FURUKAWA ELECTRIC CO., LTD.), may be used.

The system of quantitatively determining a biomolecule of the present invention, when used in fluorescent silica particles assay by flow cytometry, allows quantitative determination of plural kinds of biomolecules in only a single measurement, and is useful, for example, in quantitative determination of an extremely trace amount of analytes, such as when there is some restriction in obtaining the sample, for example during a clinical test or the like.

The system of quantitatively determining a biomolecule of the present invention, which recognizes the silica particles only by receiving the fluorescence of the silica particles, allows reduction in size, eliminating the scattered light-detection region.

The method of quantitatively determining a biomolecule of the present invention allows quantitative determination of any biomolecule by flow cytometry, although it was hitherto aimed at detecting cells.

The method of quantitatively determining a biomolecule of the present invention, which recognizes the silica particles only by receiving the fluorescence of the silica particles, does not demand the tedious operation needed in handling scattered light.

The system and the method of detecting or separating a cell of the present invention allows detection and isolation of any plural kinds of cells only in a single measurement according to the characteristics of the cellular surface layer, such as of a cancer cell surface layer, a virus-infected cell surface layer, or heterologous graft cell surface layer. It is advantageous in identifying an extremely trace amount of cells, when there is some restriction in obtaining samples for example during a clinical test.

The fluorescent silica particles used in the system of quantitatively determining a biomolecule and detecting or separating a cell of the present invention, which are inexpensive, can be modified on the surface thereof for targeting any biomolecule, cell, or the like, and also can be converted to various kinds of silica particles different in fluorescence intensity. In addition, the fluorescent silica particles are superior in resistance to photobleaching as a fluorescent material.

The multiplexing kit of the present invention, which is prepared in combination of plural kinds of fluorescent silica particles, can be used as a fluorescent material of bar-code labelling beads.

The present invention will be described in more detail based on examples given below, but the invention is not meant to be limited by these.

EXAMPLES

The present invention will be described in more detail based on examples given below, but the invention is not meant to be limited by these.

Example 1

Simultaneous Quantitative Determination of Plural Kinds of Cytokines by Using Fluorescent Silica Particles Surface-Modified with an Antibody in Flow Cytometry Hereinafter, examples of the method of preparing fluorescent silica particles and the method of quantitatively detecting plural kinds of cytokines simultaneously by using the fluorescent silica particles will be described.

(Preparation of a Fluorescein-Silane-Coupling Agent Complex)

3.3 mg of 5(6)-carboxyfluorescein-N-hydroxysuccinimide ester (manufactured by Roche) was dissolved in 1 ml of dimethylsulfoxide (DMSO). 1.3 µl of APS was added thereto, and the mixture was allowed to react at room temperature (23° C.) for 1 hour, to give a solution A.

(Preparation of DY630-Silane-Coupling Agent Complex)

5.3 mg of DY630-NHS ester (trade name, manufactured by Dyomics GmbH) was dissolved in 1 ml of DMSO. 1.3 µl of APS was added thereto, and the mixture was allowed to react at room temperature for 1 hour, to give a solution B.

(Preparation of Bar-Code Fluorescent Silica Particles Containing Two Kinds of Dyes)

The obtained solutions A and B were blended at the blending ratio shown in Table 2, and 3.95 ml of ethanol, 20 µl of MPS, 1 ml of distilled water, and 100 µl of 28 mass % aqueous ammonia were added thereto, and the mixture was allowed to react at room temperature for 24 hours.

The reaction solution was centrifuged at a gravitational acceleration of 2,000×g for 5 minutes, and the supernatant was removed. The precipitated silica particles were redispersed in 1 ml of distilled water, and centrifuged again at a gravitational acceleration of 2,000×g for 5 minutes. The washing operation was repeated twice additionally, for removal of the unreacted MPS, ammonia or the like contained in the fluorescent silica particle dispersion.

In this way, six kinds of silica particles (beads Nos. 1 to 6) at the blending ratios shown in Table 2 that are different in the contents of two dyes, 5(6)-carboxyfluorescein and DY630 were obtained.

FIG. 1 is a TEM photograph showing the fluorescent silica particle beads No. 1 obtained. Black spherical substances in the figure are the fluorescent silica particle beads No. 1 obtained. Observation of the TEM photograph of FIG. 1 confirmed that desired fluorescent silica particles were obtained.

The yields and the average diameters thereof are summarized in the following Table 3.

TABLE 2

Blending ratio of dye solution

| Beads No. | Dye solution | |
|---|---|---|
| | Solution A (μl) | Solution B (μl) |
| 1 | 5 | 0 |
| 2 | 5 | 40 |
| 3 | 15 | 0 |
| 4 | 15 | 40 |
| 5 | 40 | 0 |
| 6 | 40 | 40 |

The solution A contains 5(6)-carboxyfluorescein, and the solution B contains DY630.

TABLE 3

| Beads No. | 1 | 2 | 3 | 4 | 5 | 6 |
|---|---|---|---|---|---|---|
| Yields (%) | 12 | 17 | 15 | 14 | 17 | 13 |
| Average diameters (nm) | 981 | 970 | 935 | 1012 | 953 | 966 |

The average diameter was an average determined by selecting five different positions in the TEM photograph and 50 silica particles randomly at each position, measuring the diameters thereof, and calculating the average circle-equivalent diameter thereof at the five positions.

(Modification of Fluorescent Silica Particles with Antibody)

450 μl of a mixture of 3-sulfo-N-hydroxysuccinimide (Sulfo-NHS) and 1-ethyl-3 (3-dimethylaminopropyl)-carbodiimide (EDC) (0.05 M Sulfo-NHS, 0.2 M EDC, dissolved in phosphate-buffered saline solution (PBS)) was added to 50 μl of the No. 1 fluorescent silica particles, the mixture was agitated for 10 minutes, then 50 μl of anti-mouse IL-2 antibody (100 μg/ml) was added thereto, and the mixture was agitated additionally for 1 hour.

Silica particles were precipitated by centrifugation, and, after removal of the supernatant, the particles were dialyzed against PBS twice for removal of unreacted reagents. In this way, fluorescent silica particles carrying the anti-mouse IL-2 antibody on the surface were obtained.

(Preparation of Plural Kinds of Beads)

The fluorescent silica particles of Nos. 2 to 6 were also modified with anti-mouse IL-4 antibody, anti-mouse IL-5 antibody, anti-mouse IL-10 antibody, anti-mouse TNF-α antibody, or anti-mouse IFN-γ antibody on the surface, to give six kinds of beads carrying correspondence relationship between the kinds of beads and the antibodies shown in Table 4.

TABLE 4

| Beads No. | Modifying antibody |
|---|---|
| 1 | Anti-mouse IL-2 antibody |
| 2 | Anti-mouse IL-4 antibody |
| 3 | Anti-mouse IL-5 antibody |
| 4 | Anti-mouse IL-10 antibody |
| 5 | Anti-mouse TNF-α antibody |
| 6 | Anti-mouse IFN-γ antibody |

(Antigen-Antibody Reaction on Silica Particle)

Samples respectively containing 5 μg/ml of IL-2, IL-4, IL-5, IL-10, TNF-α, and IFN-γ were prepared as cytokine standard samples. Each sample was diluted to 1/2, 1/4, 1/8, 1/16, 1/32, 1/64, 1/128, and 1/256, to give nine kinds of diluted standard samples.

The six kinds of antibody-modified silica particles were mixed in PBS. The bead liquid mixture obtained was placed in 10 microtubes each in a portion of 50 μl.

50 μl of a solution containing respectively 20 μg/ml of PE (phycoerythrin)-labelled anti-IL-2 antibody, PE-labelled anti-IL-4 antibody, PE-labelled anti-IL-5 antibody, PE-labelled anti-IL-10 antibody, PE-labelled anti-TNF-α antibody, and PE-labelled anti-IFN-γ antibody (respectively antibodies binding to an epitope other than the antibody bound to the silica particle surface) were added thereto, as labelled probes for quantitative determination.

Then, 50 μl of one kind of standard sample was added to 9 microtubes among these 10 microtubes, and 50 μl of mouse blood serum to the one remained microtube, 350 μl of PBS was added to respective microtubes, and the mixtures were allowed to react at room temperature for 3 hours.

After reaction, silica particles were sedimented by centrifugation, and the supernatant was removed. 500 μl of PBS was added thereto, and the silica particles were dispersed and then sedimented by centrifugation again and the supernatant was removed, to thereby wash the silica particles.

(Measurement on a Flow Cytometer and Quantitative Determination of Cytokine)

After washing, 500 μl of PBS was added for dispersion of the silica particles. 100 μl of the dispersion above was placed in a test tube and diluted with 2 ml of Assay Diluent (trade name, manufactured by Becton, Dickinson and Company). The solution was analyzed with FACS Calibur (trade name, manufactured by Becton, Dickinson and Company). 10,000 Particles were analyzed by using two kinds of fluorescence excitation laser (488 nm and 635 nm).

A two-dimensional dot plot of two kinds of fluoescences (488 nm—excited fluorescence at 530 nm (FL1) and 635 nm—excited fluorescence at 670 nm (FL3)) was first made from the measurement data.

Figure 2:
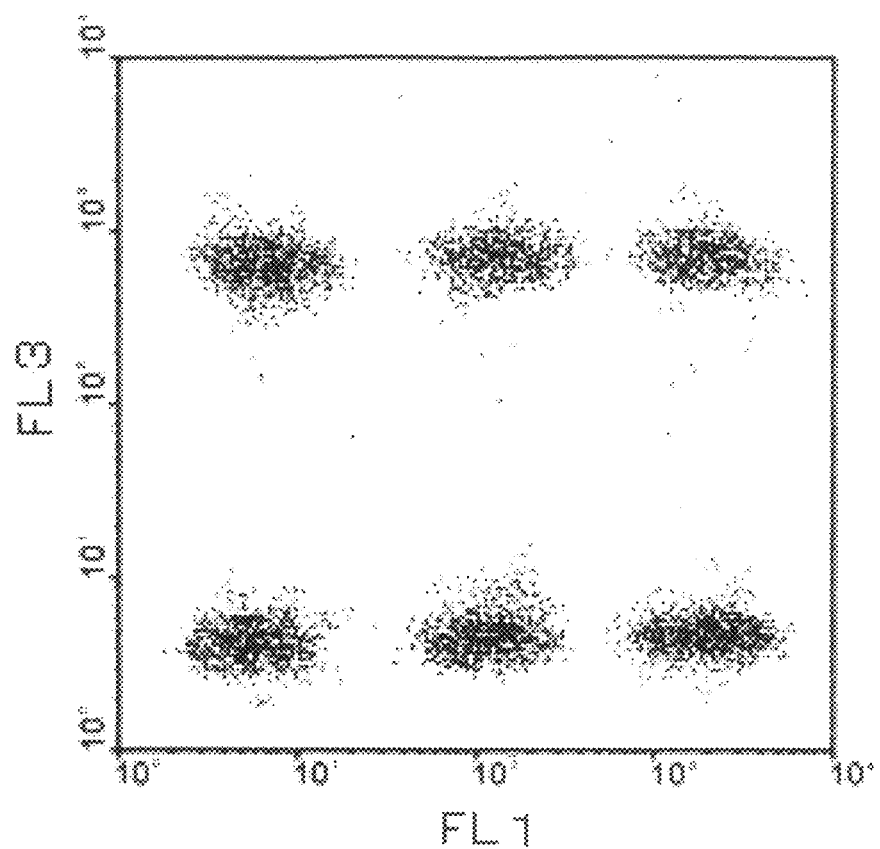
FIG. 2 is a two-dimensional dot plot showing the intensity of 488 nm-excited fluorescence at 530 nm (FL1 channel detection) and the intensity of 635 nm-excited fluorescence at 670 nm (FL3 channel detection).

FIG. 2 is a chart showing the two-dimensional dot plot of the 488 nm-excited fluorescence at 530 nm (FL1) and 635 nm-excited fluorescence at 670 nm (FL3).

As is apparent from FIG. 2, bar-code labelling of the fluorescent silica particles (beads) of the present invention enabled differentiation of six kinds of cytokines (IL-2, IL-4, IL-5, IL-10, TNF-α and IFN-γ).

For quantitative determination of each cytokine, gates were installed for separation of the mixed data of the six kinds of fluorescent silica particles into individual data.

Figure 3:
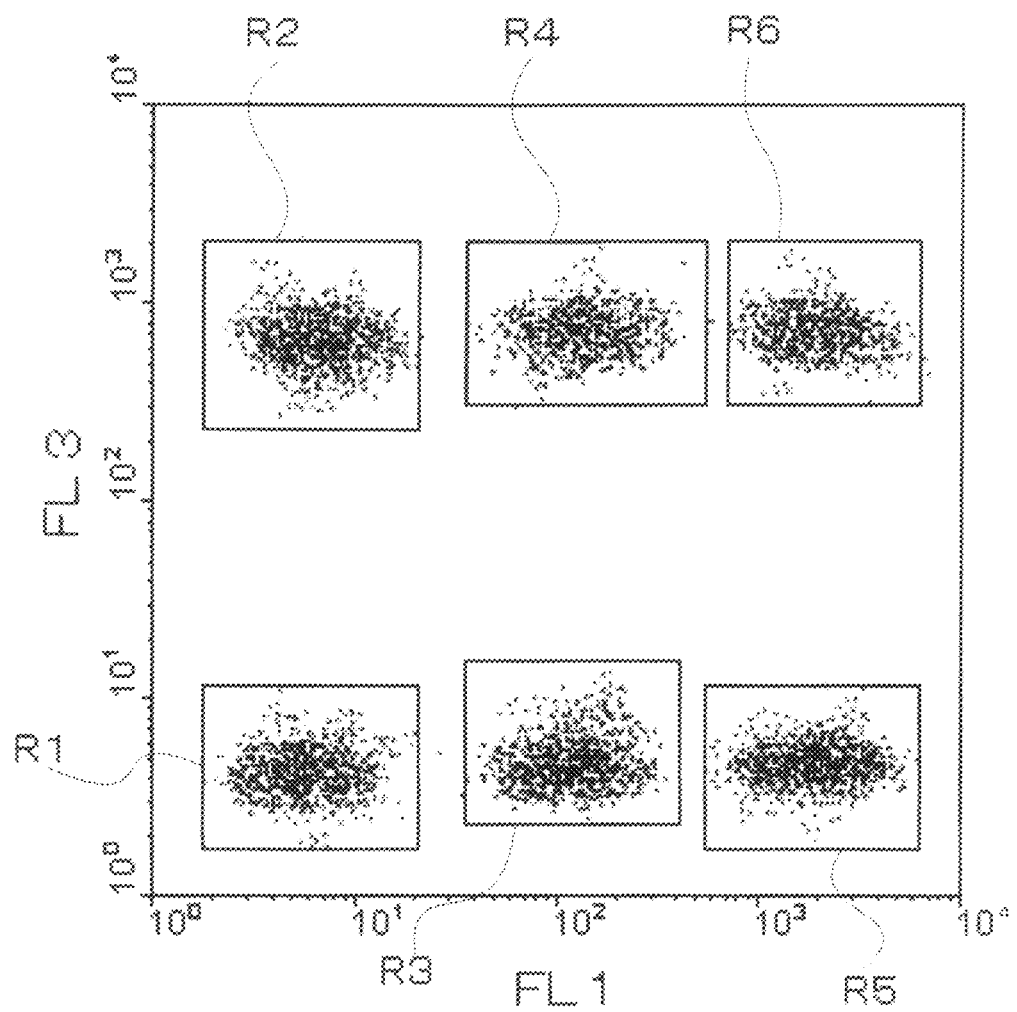
FIG. 3 is a two-dimensional dot plot of FIG. 2 divided into six kinds of gates.

FIG. 3 is a chart showing the two-dimensional dot plot of FIG. 2 with six kinds of gates shown thereon. In FIG. 3, R1, R2, R3, R4, R5 and R6 each represent a gate.

The following Table 5 summarized the relationship between the beads No. and the gate.

TABLE 5

| Beads No. | Gate |
|---|---|
| 1 | R1 |
| 2 | R2 |
| 3 | R3 |
| 4 | R4 |
| 5 | R5 |
| 6 | R6 |

Subsequently, the fluorescence intensity of phycoerythrin per bead was calculated, from the data on the number of each silica particles and the fluorescence intensity (FL2) of the 488 nm-excited fluorescence at 585 nm derived from the probe for quantitative determination.

Figure 4:
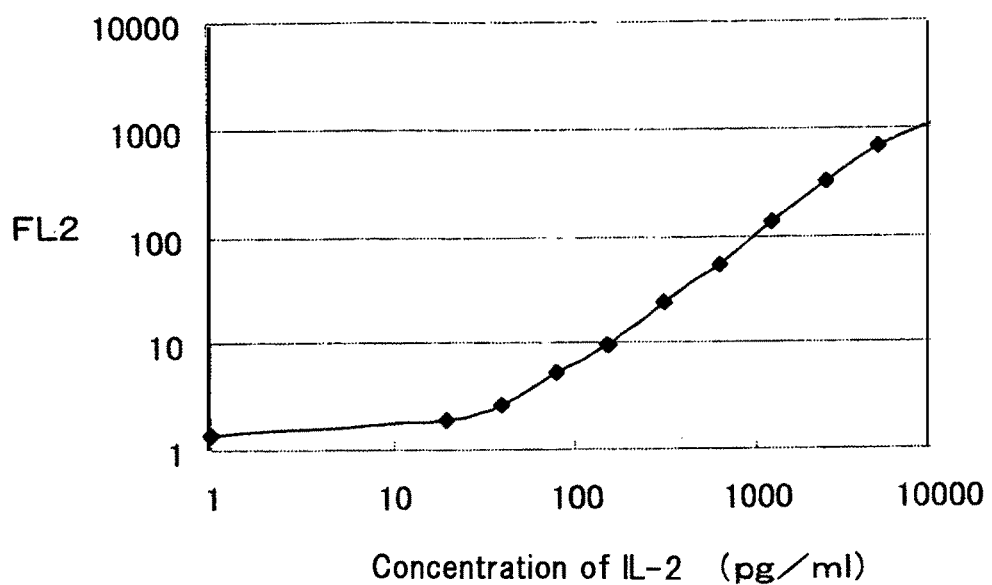
FIG. 4 is a calibration curve showing the relationship between the IL-2 concentration and the phycoerythrin fluorescence intensity (FL2 channel detection).

FIG. 4 is the calibration curve showing the relationship between the FL2 count to the IL-2 concentration.

Calibration curves for other cytokines (IL-4, IL-5, IL-10, TNF-α and IFN-γ) were also drawn similarly to IL-2, from the relationship between the cytokine concentration and the fluorescence intensity (FL2 channel detection) of phycoerythrin per silica particle obtained from the 9 kinds of standard samples different in concentration.

The concentrations of six kinds of cytokines contained in a mouse blood serum sample were calculated from the calibration curve between the FL2 intensity and each cytokine concentration and also the calibration curves for other cytokines shown in FIG. 4.

The quantitative determination test of the cytokines was repeated six times by using the same mouse blood serum sample. The average value of the concentration of each cytokine and the CV value, as determined by the six measurements, are summarized in Table 6.

TABLE 6

| Cytokine | IL-2 | IL-4 | IL-5 | IL-10 | TNF-α | IFN-γ |
|---|---|---|---|---|---|---|
| Average concentration (pg/ml) | 0.39 | 0.88 | 0.61 | 0.18 | 1.03 | 1.12 |
| %CV | 8% | 6% | 8% | 9% | 6% | 5% |

As is apparent from the results shown in Table 6, it was possible to determine six kinds of cytokines in mouse blood serum quantitatively in a single flow cytometric operation.

Example 2

Preparation of Fluorescent Silica Particles for Labelling a Cell

A fluorescein-silane-coupling agent complex was first prepared, in a similar manner to Example 1.

Specifically, 3.3 mg of 5(6)-carboxyfluorescein-N-hydroxysuccinimide ester (manufactured by Roche) was dissolved in 1 ml of dimethylsulfoxide (DMSO). 1.3 μl of APS was added thereto, and the mixture was allowed to react at room temperature (23° C.) for 1 hour, to give a solution of the fluorescein-silane-coupling agent complex.

Subsequently, 6.4 ml of ethanol, 1.6 ml of distilled water, and 100 μl of 28 mass % aqueous ammonia were mixed with each other, and 40 μl of the fluorescein-silane-coupling agent complex and 20 μl of TEOS were added thereto, and the mixture was allowed to react at room temperature for 24 hours.

The reaction solution was centrifuged at a gravitational acceleration of 22,000×g for 30 minutes, and the supernatant was removed. 1 ml of distilled water was added to the precipitated silica particle for dispersion, and the dispersion was centrifuged again at a gravitational acceleration of 22,000×g for 30 minutes. Further, the washing operation was repeated twice additionally, for removal of the unreacted TEOS, ammonia and others contained in the fluorescent silica particle dispersion, to give 5(6)-carboxyfluorescein-containing silica particles (average diameter: 39 nm). The yield was 48%.

Figure 5:
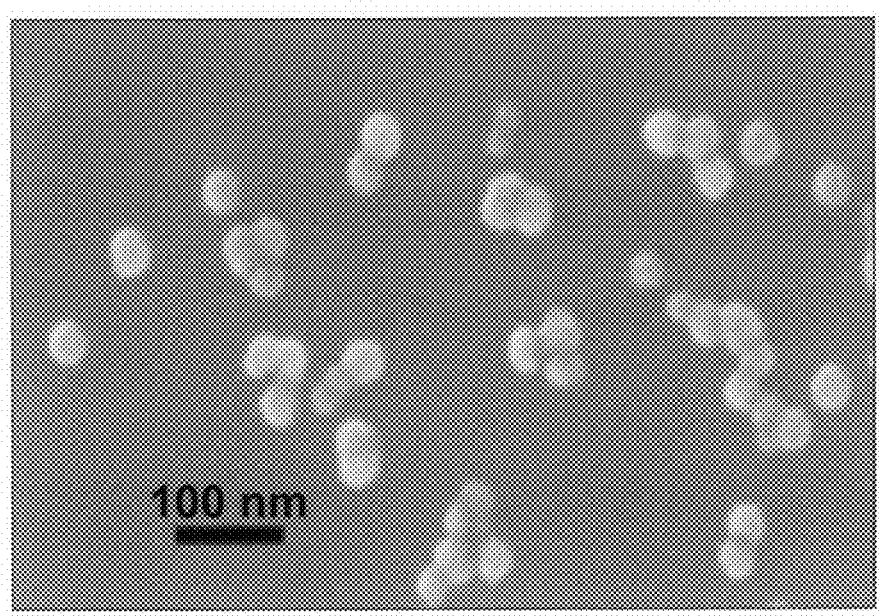
FIG. 5 is a SEM photograph of the fluorescent silica particles obtained.

FIG. 5 is a SEM photograph showing the obtained beads of the fluorescent silica particles bead obtained. In the Figure, white spherical substances correspond to the fluorescent silica particle beads obtained. Observation of the SEM photograph of FIG. 5 confirmed that fluorescent silica particles were obtained.

1 ml of 50 mM $KH_2PO_4$ (pH 6.5) was added to and mixed slightly with 9 ml of the fluorescent silica particle dispersion (2 mg/ml, dispersion in distilled water). 1 ml of a 60 μg/ml anti-mouse CD4 antibody dissolved in distilled water was added thereto, and the mixture was left still at room temperature for 10 minutes. 1.1 ml of 10% BSA was then added, and the mixture was agitated slightly.

The dispersion was centrifuged at a gravitational acceleration of 8,000×g for 30 minutes, and the supernatant was removed. 20 ml of 20 mM Tris (hydroxymethyl)aminomethane (pH 8.0) was added thereto for dispersion of the particles. The dispersion was centrifuged again at a gravitational acceleration of 8,000×g for 30 minutes, the supernatant was removed, and 2 ml of 20 mM Tris (hydroxymethyl) aminomethane (pH 8.0) was added thereto, for dispersion of the particles, to give a dispersion of the fluorescent silica particles modified with an anti-mouse CD4 antibody (8.2 mg/ml×2 ml).

Example 3

Labelling of Mouse Splenic Cell with Fluorescent Silica Particles

Mouse splenic cells are collected from exenterated spleens of three mice. The mouse splenic cells were washed with 0.1% BSA (bovine serum albumin)-containing PBS once and then centrifuged for removal of the supernatant. 10 ml of a tris buffer solution (ACTB) for removal of erythrocytes was added thereto, the mixture was agitated by pipetting, left still for 5 minutes, and then, subjected to erythrocyte decomposition treatment. Subsequently, the mixture was diluted with 20 ml of 0.1% BSA-containing PBS and centrifuged for removal of the supernatant, the splenic cells thus obtained were washed with 0.1% BSA-containing PBS twice and redispersed in 5 ml of 0.1% BSA-containing PBS. 100 μl of a dispersion containing fluorescent silica particles modified with an anti-mouse CD4 antibody was added to 500 μl of the mouse splenic cell dispersion thus obtained, and the mixture was allowed to react in antigen-antibody reaction at 0° C. for 3 hours.

After reaction, the mouse splenic cells were washed with 0.1% BSA-containing PBS twice and redispersed in 500 μl of 0.1% BSA-containing PBS.

The mouse splenic cell dispersion obtained was analyzed by using a flow cytometer.

Figure 6:
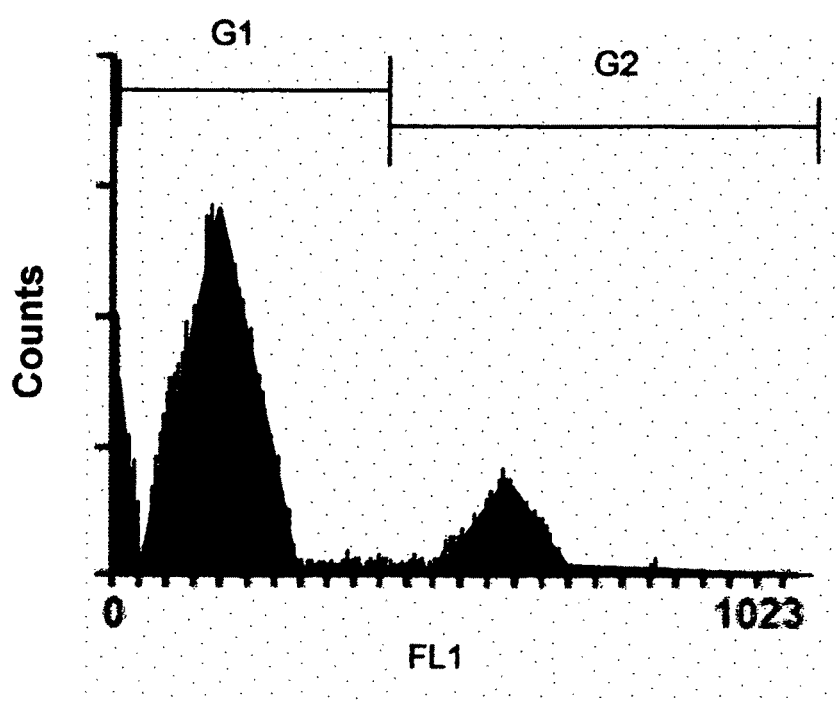
FIG. 6 is a histogram showing the measurement results of the flow cytometry in Example 3, as the intensity of the 488 nm-excited fluorescence at 530 nm (FL1) and the count are plotted respectively on the abscissa and the ordinate.

FIG. 6 is a histogram showing the measurement results above, as the intensity of the 488 nm-excited fluorescence at 530 nm (FL1) and the count respectively plotted on the abscissa and the ordinate. In FIG. 6, the region of gate 1 (G1) where the fluorescence intensity is weaker, indicates the count of the CD4-negative cells, while the region of gate 2 (G2), where the fluorescence intensity is stronger, indicates the count of the fluorescent silica particles labeling CD4-positive cell. The histogram confirmed that approximately 20% of the cells were CD4-positive cells.

INDUSTRIAL APPLICABILITY

The system and the method of quantitatively determining a biomolecule of the present invention allow simultaneous quantitative determination of plural kinds of target biomolecules in a single measurement operation by flow cytometry. In addition, the targets are not limited to biomolecules, and thus, provided are a system and a method allowing simultaneous detection and separation of plural kinds of cells. Also provided are fluorescent materials, for example a set in combination of plural kinds of fluorescent silica particles, for flow cytometry enabling simultaneous quantitative determination, detection and separation of plural kinds of biomolecules and cells, as described above.

Having described our invention as related to the present embodiments, it is our intention that the invention not be limited by any of the details of the description, unless otherwise specified, but rather be construed broadly within its spirit and scope as set out in the accompanying claims.

The invention claimed is:

1. A method of quantitatively determining a target biomolecule in flow cytometry, comprising the steps of:
   providing plural kinds of target biomolecules, wherein the target biomolecules are labeled with fluorescence A for quantitative determination of the target biomolecules;
   providing plural kinds of different fluorescent silica particles having an average diameter of 300 nm to 1200 nm, wherein the different fluorescent silica particles are optionally substantially uniform in particle diameter,
   wherein each kind of fluorescent silica particles is capable of emitting individual fluorescence B, detectable by a flow cytometer, each of the plural kinds of silica particles having dyes different in kinds and/or ratios differing in fluorescence emission spectrum and/or having a fluorescence intensity in plural phases, wherein fluorescence A emits fluorescence at a different wavelength from fluorescence B emitted by each of the fluorescent silica particles;
   wherein each kind of the fluorescent silica particles is surface-coated with a binding substance capable of distinguishably immobilizing each kind of the fluorescence A labeled target biomolecules;
   immobilizing each kind of the fluorescence A labeled target biomolecules on the surface of the corresponding kind of fluorescent silica particles via the binding substance; and
   distinguishably detecting signals from each one of the individual plural kinds of fluorescent silica particles emitting fluorescence B, and
   detecting an intensity of the fluorescence A from each kind of the labeled target biomolecules, to determine a quantity of each kind of target biomolecule, by using the flow cytometer.

2. The method of quantitatively determining a biomolecule according to claim 1, wherein plural kinds of target biomolecules are simultaneously quantitated.

3. The method of quantitatively determining a biomolecule according to claim 1, wherein the fluorescence emitted from the fluorescent silica particles is resistant to photobleaching.

4. The method of quantitatively determining a biomolecule according to claim 1, further comprising obtaining detection data from each of the fluorescent silica particles that capture the target biomolecules, and differentiating and bar-code labeling each kind of fluorescent silica particles.

5. The method of quantitatively determining a biomolecule according to claim 1, wherein the plural kinds of target biomolecules are selected from the group consisting of an antigen, an antibody, a DNA, a RNA, a sugar, a polysaccharide and a peptide.

6. The method of quantitatively determining a biomolecule according to claim 1, wherein the fluorescent silica particles are distinguished in each kind by using bar-code labeling.

7. The method of quantitatively determining a biomolecule according to claim 1, wherein the fluorescent dye is contained in the fluorescent silica particle in an amount of 5-60 mmol/L.

8. The method of quantitatively determining a biomolecule according to claim 1, wherein the binding substance coated onto each kind of fluorescent silica particle is selected from the group consisting of an antibody, an antigen, a peptide, a DNA, a RNA, a polysaccharide, and a receptor.

9. The method of quantitatively determining a biomolecule according to claim 1, Wherein the quantity of the target biomolecule is calculated from a calibration curve between the intensity of fluorescence A and the amount of the biomolecule.

10. The method of quantitatively determining a biomolecule according to claim 1, wherein each of the plural kinds of silica particles having dyes different in kinds and/or ratios comprise two to four kinds of fluorescent dye compounds.

11. The method of quantitatively determining a biomolecule according to claim 1, wherein each of the plural kinds of silica particles have a fluorescence intensity in plural phases because of differences in a content of the fluorescent dye compounds contained in each silica particle.

12. A method of quantitatively determining a target biomolecule in flow cytometry, comprising the steps of:
   providing plural kinds of target biomolecules;
   providing plural kinds of different fluorescent silica particles having an average diameter of 300 nm to 1200 nm, wherein the different fluorescent silica particles are optionally substantially uniform in particle diameter,
   wherein each kind of fluorescent silica particles is capable of emitting individual fluorescence B, detectable in a flow cytometer, each of the plural kinds of silica particles having dyes different in kinds and/or ratios differing in fluorescence emission spectrum and/or having a fluorescence intensity in plural phases, wherein each kind of the fluorescent silica particles is surface-coated with a binding substance capable of distinguishably immobilizing each kind of the target biomolecules;
   providing fluorescent-labeled probes, each labeled probe capable of emitting fluorescence A for quantitative determination of the target biomolecules, the fluorescent-labeled probes specifically capable of binding to the plural kinds of target biomolecules respectively, wherein fluorescence A emits fluorescence at a different wavelength from fluorescence B emitted by each of the fluorescent silica particles;
   immobilizing each kind of the target biomolecules on the surface of the corresponding kind of fluorescent silica particles;
   mixing the fluorescent-labeled probes with the fluorescent silica particles; and
   distinguishably detecting signals from each one of the individual plural kinds of fluorescent silica particles emitting fluorescence B, and detecting an intensity of the fluorescence A from each of the fluorescent-labeled probes to determine a quantity of each kind of target biomolecule, by using the flow cytometer.

13. A method of quantitatively determining a biomolecule, comprising the steps of:
   providing plural kinds of target biomolecules;
   providing plural kinds of different fluorescent silica particles having an average diameter of 300 nm to 1200 nm, wherein the different fluorescent silica particles are optionally substantially uniform in particle diameter,
   wherein each kind of fluorescent silica particles is capable of emitting individual fluorescence B, detectable in a flow cytometer, each of the plural kinds of silica particles having dyes different in kinds and/or ratios differing in fluorescence emission spectrum and/or having a fluorescence intensity in plural phases, wherein each kind of the fluorescent silica particles is surface-coated with a binding substance capable of distinguishingly immobilizing each kind of the target biomolecules;

providing at least two kinds of molecular recognition substances capable of specifically binding to the plural kinds of target biomolecules respectively;

providing fluorescent-labeled probes, each labeled probe capable of emitting fluorescence A for quantitative determination of the target biomolecules, the fluorescent-labeled probes specifically capable of binding to the at least two molecular recognition substances respectively, wherein fluorescence A emits fluorescence at a different wavelength from fluorescence B emitted by each of the fluorescent silica particles;

mixing the molecular recognition substances with the plural kinds of fluorescent silica particles;

mixing the fluorescent-labeled probes with the plural kinds of fluorescent silica particles; and distinguishably detecting signals from each one of the individual plural kinds of fluorescent silica particles emitting fluorescence B, and detecting an intensity of the fluorescence A from each of the fluorescent-labelled probes to determine a quantity of each kind of target biomolecule, by using the flow cytometer.

14. The method of quantitatively determining a biomolecule according to claim 12 or 13, wherein the fluorescent-labeled probe comprises fluorescent silica particles surface-coated with a binding substance capable of specifically binding to the target biomolecules or the molecular recognition substances.

15. The method of quantitatively determining a biomolecule according to claim 12 or 13, wherein the molecular recognition substance is at least one selected from the group consisting of an antigen, an antibody, a DNA, a RNA, a sugar, a polysaccharide, a ligand, a receptor, a peptide and a chemical substance.

* * * * *